(12) United States Patent
Tseng et al.

(10) Patent No.: US 12,329,864 B2
(45) Date of Patent: Jun. 17, 2025

(54) COSMETIC TREATMENT

(71) Applicant: A-TOP Health BIOTECH CO., LTD., Taipei (TW)

(72) Inventors: Yu-Chia Tseng, Taipei (TW); Ping-Chuan Chen, Taipei (TW)

(73) Assignee: A-TOP HEALTH BIOTECH CO., LTD., Taipei (TW)

( * ) Notice: Subject to any disclaimer, the term of this patent is extended or adjusted under 35 U.S.C. 154(b) by 0 days.

(21) Appl. No.: 18/657,158

(22) Filed: May 7, 2024

(65) Prior Publication Data

US 2024/0390549 A1 Nov. 28, 2024

Related U.S. Application Data

(62) Division of application No. 18/222,618, filed on Jul. 17, 2023, now Pat. No. 12,053,553.

(30) Foreign Application Priority Data

May 24, 2023 (TW) .................................. 112119261

(51) Int. Cl.
*A61L 17/06* (2006.01)
*D02G 3/44* (2006.01)

(52) U.S. Cl.
CPC .............. *A61L 17/06* (2013.01); *D02G 3/449* (2013.01)

(58) Field of Classification Search
CPC ................................ A61L 17/06; D02G 3/449
See application file for complete search history.

(56) References Cited

U.S. PATENT DOCUMENTS

| | | | |
|---|---|---|---|
| 5,044,013 A | 9/1991 | Ackerman | |
| 7,816,288 B2 | 10/2010 | Leonard et al. | |
| 10,492,780 B2 * | 12/2019 | Gross | A61B 17/0485 |
| 12,194,192 B2 * | 1/2025 | Shen | A61L 27/26 |
| 2004/0187471 A1 | 9/2004 | Andrews et al. | |
| 2006/0099866 A1 | 5/2006 | Leonard et al. | |
| 2007/0271682 A1 | 11/2007 | Eastman, II | |
| 2012/0246797 A1 | 10/2012 | Montgomery et al. | |
| 2013/0012090 A1 | 1/2013 | Leonard et al. | |
| 2013/0018393 A1 * | 1/2013 | Bengtson | A61B 17/0644 606/139 |
| 2014/0088700 A1 | 3/2014 | Mortarino et al. | |
| 2015/0142052 A1 | 5/2015 | Koogle, Jr. et al. | |

(Continued)

FOREIGN PATENT DOCUMENTS

CN 115105647 A 9/2022
TW 202203856 A 2/2022

*Primary Examiner* — Phong Son H Dang
(74) *Attorney, Agent, or Firm* — Birch, Stewart, Kolasch & Birch, LLP

(57) ABSTRACT

The present invention provides a surgical thread, comprising a modified cross-section fiber, wherein the modified cross-section fiber is in a twisted state. The surgical thread of the present invention has advantages of good coefficient of kinetic friction, good tensile strength, good elongation rate and good softness, and good safety, comprising no inflammatory potential, no cytotoxicity, no pyrogen, no acute systemic toxicity and no intradermal irritation potential, and has the efficacy of promotion of collagen formation, thereby being suitable for embedding in the face. The present invention further provides a cosmetic treatment and a manufacturing method for the surgical thread.

17 Claims, 12 Drawing Sheets

(56) References Cited

U.S. PATENT DOCUMENTS

| | | |
|---|---|---|
| 2018/0100265 A1 | 4/2018 | Gang |
| 2020/0362485 A1 | 11/2020 | Kanematsu et al. |
| 2021/0310159 A1* | 10/2021 | Mandawewala ....... C08K 11/00 |
| 2022/0031316 A1 | 2/2022 | Chang et al. |
| 2022/0056619 A1 | 2/2022 | Owens, Jr. et al. |
| 2022/0074086 A1 | 3/2022 | Todo et al. |
| 2022/0235496 A1 | 7/2022 | Inoue et al. |
| 2023/0313419 A1* | 10/2023 | Mandawewala ........ D01F 6/605 |
| | | 424/404 |
| 2024/0423611 A1* | 12/2024 | Balaji .............. A61B 17/06166 |

\* cited by examiner blank negative control positive control

Example 2-6

Comparative Example 2

COSMETIC TREATMENT

CROSS-REFERENCE TO RELATED APPLICATION

Pursuant to 35 U.S.C. § 119 (a), this application claims the benefits of the priority to Taiwan Patent Application No. 112119261, filed on May 24, 2023, which is incorporated by reference herein in its entirety.

BACKGROUND OF THE INVENTION

1. Field of the Invention

The present invention relates to a surgical thread, especially a surgical thread for embedding within the face. The present invention further relates to a cosmetic treatment using the surgical thread and a manufacturing method for the surgical thread.

2. Description of the Prior Arts

Modern people are involved in social activities more frequently with ever increasing awareness to personal appearance, thereby making the beauty industry flourish. In comparison with daily skin care such as topically applying skin care products, cosmetic surgery can achieve appearance modification efficacy more directly and more rapidly, thereby becoming more and more popular. Taking a sagging face resulting from aging as an example, "thread lifting" is a surgery that fixes an implant thread in the subcutaneous fat layer and superficial muscular aponeurotic system (SMAS) layer temporarily to support and remodel the facial tissue, thereby achieving an immediate face-lifting efficacy.

The commercial surgical threads for embedding or lifting currently available are single-strand round threads, the surfaces of which are incised section by section to form various barb structures; or a fish bone or a zigzag structure is obtained by molding section by section, thereby providing a capacity to anchor or maintain in the target tissue. However, according to clinical feedbacks, the commercial surgical threads for embedding or lifting currently available often bring a foreign body sensation, or are prone to injure the target tissue, which further results in a potential risk of triggering a severe immune response. Therefore, a surgical thread for embedding or lifting which better meets consumers' needs are yet to be developed.

SUMMARY OF THE INVENTION

To solve the aforementioned problem, the present invention provides a surgical thread, comprising a modified cross-section fiber, wherein the modified cross-section fiber is in a twisted state.

The term "modified cross-section fiber" refers to a fiber with a cross section that is "non-circular." The term "cross section" refers to the transverse cross-section perpendicular to the longitudinal direction of the fiber. In comparison with the ordinary fibers which are circular cross-section fibers, the surface area per unit length of the modified cross-section fiber adopted in the present invention is larger and can be at least 20% larger than that of the circular cross-section fiber, which increases the contact area between the surgical thread of the present invention and target cells in the tissue, thereby improving the efficacy of cell adhesion and proliferation. Furthermore, the twisted state of the modified cross-section fiber of the present invention can further increase the degree of unevenness on the surface of the surgical thread of the present invention and the friction force thereof along the longitudinal direction as well. By improving the surface roughness of the surgical thread of the present invention, the surgical thread of the present invention has a high coefficient of kinetic friction, which can be at least 24% higher than that of the circular cross-section fiber, thereby further improving its capacity for the adhesion of target cells in the tissue to improve cell adhesion and proliferation.

Further, in comparison with the commercial surgical threads for embedding or lifting with various barb structures, a fish bone or a zigzag structure, the modified cross-section fiber in a twisted state of the present invention has no sharp or obvious protrusions, which can reduce a foreign body sensation and the risk of triggering a severe immune response due to tissue injury. Finally, in comparison with the fibers per se, barbs, a fish bone or a zigzag structure are each thinner and more vulnerable for digestion, and have difficulties adhering to or staying in the tissue for a long period. Since both the modified cross-section fiber of the present invention and the twisted state thereof are fibers per se, which are thicker than barbs, a fish bone or a zigzag structure, the surgical thread of the present invention has the advantage of adhering to or staying in the tissue for a longer period.

In one embodiment, based on the length of the circumference of the cross-section of a circular cross-section fiber, which is indicated as 1, the length of the circumference of the cross-section of the modified cross-section fiber is greater than 1. That is, the length of the circumference of the cross-section of the modified cross-section fiber is greater than that of a circular cross-section fiber; subject to that both the diameter of the cross-section of the circular cross-section fiber and the longest diameter of the cross-section of the modified cross-section fiber have the same length.

In one embodiment, the modified cross-section fiber has a cross-section of a cross shape, a Y shape, a Union Jack shape or a multi-leaf shape. Preferably, the multi-leaf shape comprises a four-leaf shape or a five-leaf shape.

In one embodiment, the modified cross-section fiber has an ingredient of a biodegradable material. Preferably, the biodegradable material comprises polydioxanone (PDO), poly(L-lactide-co-caprolactone) (PLC), poly(L-lactide) (PLLA) or poly(glycolide-co-L-lactide) (PGL).

In one embodiment, polydioxanone is poly(p-dioxanone).

According to the present invention, the ingredients of the modified cross-section fiber are biodegradable materials, and it is confirmed that the surgical thread has no inflammatory potential, no cytotoxicity, no pyrogen, no acute systemic toxicity and no intradermal irritation potential.

In one embodiment, the inherent viscosity (IV) of the raw material of the polydioxanone is 1.5 dl/g to 2.2 dl/g; the inherent viscosity of the raw material of the poly(L-lactide-co-caprolactone) is 1.3 dl/g to 1.8 dl/g; the inherent viscosity of the raw material of the poly(L-lactide) is 3.3 dl/g to 4.3 dl/g; the inherent viscosity of the raw material of the poly(glycolide-co-L-lactide) is 1.05 dl/g to 1.25 dl/g.

In one embodiment, for poly(L-lactide-co-caprolactone), based on the total moles of L-lactide and caprolactone, L-lactide is in an amount of 60 molar percent to 80 molar percent, and caprolactone is in an amount of 20 molar percent to 40 molar percent. Preferably, based on the total moles of L-lactide and caprolactone, L-lactide is in an amount of 65 molar percent to 75 molar percent, and caprolactone is in an amount of 25 molar percent to 35 molar percent.

In one embodiment, for poly(glycolide-co-L-lactide), based on the total moles of glycolide and L-lactide, glycolide is in an amount of 50 molar percent to 95 molar percent, and L-lactide is in an amount of 5 molar percent to 50 molar percent. Preferably, based on the total moles of glycolide and L-lactide, glycolide is in an amount of 80 molar percent to 95 molar percent, and L-lactide is in an amount of 5 molar percent to 20 molar percent. More preferably, based on the total moles of glycolide and L-lactide, glycolide is in an amount of 87 molar percent to 93 molar percent, and L-lactide is in an amount of 7 molar percent to 13 molar percent.

In one embodiment, the modified cross-section fiber further comprises an additive. Preferably, the additive comprises an antibacterial ingredient, an active ingredient or a combination thereof.

In one embodiment, the antibacterial ingredient comprises chlorhexidine or triclosan; and/or the active ingredient comprises epidermal growth factor (EGF) or growth hormone (GH).

In one embodiment, the modified cross-section fiber absorbs platelet-rich plasma (PRP).

In one embodiment, the modified cross-section fiber has a fiber inner diameter and a fiber outer diameter, and the ratio of the fiber inner diameter to the fiber outer diameter is 0.1 to 0.95. Preferably, the ratio of the fiber inner diameter to the fiber outer diameter is 0.2 to 0.8, for example, 0.2, 0.3, 0.4, 0.5, 0.6, 0.7 or 0.8. More preferably, the ratio of the fiber inner diameter to the fiber outer diameter is 0.28 to 0.34. According to the present invention, the modified cross-section fiber with such ratio of the fiber inner diameter to the fiber outer diameter has advantages as follows: (1) facilitating the subsequent twisting process; (2) effectively balancing the mechanical strength of the surgical thread and the demand of a space reserved for cell adhesions in the tissue (the reserved space substitutes some part of the fiber per se, and will lower the mechanical strength of the surgical thread); and (3) reserving a space for the additives to be provided to the modified cross-section fiber.

The cross section of the modified cross-section fiber can be divided into a central region and at least one arm region; wherein the central region is a first imaginary circle, and at least one arm region is the part beyond the central region (the first imaginary circle). Further, among all the straight lines between the terminals of the at least one arm region and the center of the first imaginary circle, the longest straight line is chosen for drawing a second imaginary circle. Finally, the fiber inner diameter is obtained by measuring the longest diameter of the first imaginary circle, and the fiber outer diameter is obtained by measuring the diameter of the second imaginary circle.

In one embodiment, the twisted state has a twisting direction of a clockwise direction, a counterclockwise direction or a combination thereof. Preferably, a twisting direction of the twisted state is defined according to the cross section of the modified cross-section fiber; wherein the cross section of the modified cross-section fiber faces the direction opposite to the gravity of the earth.

In one embodiment, the modified cross-section fiber has a plurality of sections that are each in a twisted state, and the sections that are each in a twisted state have the same twisting direction, different twisting directions or a combination thereof.

In one embodiment, the twisted state is obtained by twisting the modified cross-section fiber.

In one embodiment, the twisting direction comprises a Z-twist, an S-twist or a combination thereof.

The Z-twist is a regular twist and indicates that the rotation direction of the twisting spindle is clockwise; and the S-twist is a reverse twist and indicates that the rotation direction of the twisting spindle is counterclockwise.

In one embodiment, the surgical thread has an amount of twist of 10 TPM (twist per meter) to 1500 TPM. Preferably, the amount of twist of the surgical thread is 300 TPM to 800 TPM. More preferably, an amount of twist of the surgical thread is 450 TPM to 550 TPM.

In one embodiment, the surgical thread is obtained by twisting a single strand or a plurality of strands of the modified cross-section fibers. Preferably, the surgical thread is obtained by twisting a single strand of the modified cross-section fiber.

In one embodiment, the surgical thread comprises a plurality of segments. Preferably, the segments are each from 0.5 cm to 60 cm, for example, 0.5 cm, 1 cm, 2 cm, 5 cm, 10 cm, 20 cm, 30 cm, 40 cm, 50 cm or 60 cm. More preferably, the segments comprise both a segment in a twisted state and a segment in an untwisted state simultaneously, or the segments that are in a twisted state with the same or different twisting directions.

In one embodiment, the surgical thread has a coefficient of kinetic friction of equal to or more than 0.35. Specifically, when the modified cross-section fiber comprises polydioxanone (PDO), the coefficient of kinetic friction of the surgical thread is 0.42 to 0.44; when the modified cross-section fiber comprises poly(L-lactide-co-caprolactone) (PLC), the coefficient of kinetic friction of the surgical thread is 0.41 to 0.43; and/or when the modified cross-section fiber comprises poly(glycolide-co-L-lactide) (PGL), the coefficient of kinetic friction of the surgical thread is 0.35 to 0.37. Preferably, a cross section of the modified cross-section fiber is in a cross shape. According to the present invention, in comparison with the ordinary fibers which are circular cross-section fibers, the modified cross-section fiber adopted by the present invention can increase the contact area and adhesion between the surgical thread and target cells in the tissue, thereby improving the efficacy of cell adhesion and proliferation for enhancing the cosmetic efficacy of lifting.

The coefficient of kinetic friction is obtained by a standard test method of ASTM D3108/D3108M-13 (Standard Test Method For Coefficient Of Friction, Yarn To Solid Material). Specifically, the present invention uses a yarn friction tester to measure the coefficient of kinetic friction of the target thread against the friction plate (a metal wheel) at a speed of 5 m/min. Preferably, the yarn friction tester is a portable mechanical yarn friction tester purchased from Standard International Group (HK) Limited. More preferably, the specification of the target thread is that: (1) the fiber outer diameter of the target thread is 0.300 mm to 0.349 mm; (2) the amount of twist of the target thread is 450 TPM to 550 TPM (twist per meter); and (3) the target thread is twisted from a single strand of the modified cross-section fiber.

In one embodiment, the surgical thread has a density of 0.1 g/cm$^3$ to 1.1 g/cm$^3$. Preferably, the density of the surgical thread is 0.3 g/cm$^3$ to 1.0 g/cm$^3$, for example, 0.3 g/cm$^3$, 0.4 g/cm$^3$, 0.5 g/cm$^3$, 0.6 g/cm$^3$, 0.7 g/cm$^3$, 0.8 g/cm$^3$, 0.9 g/cm$^3$ or 1.0 g/cm$^3$. More preferably, the density of the surgical thread is 0.58 g/cm$^3$ to 0.62 g/cm$^3$. The commercial surgical threads for embedding or lifting are circular cross-section fibers, and the density of the circular cross-section fiber is about 1.2 g/cm$^3$ to 1.5 g/cm$^3$, which is significantly higher than that of the surgical thread of the present invention. As the surgical thread of the present invention has an advantage for being lighter, the surgical thread of the present invention can reduce the weight burden on the face of the patients after implantation. Further, the surgical thread of the present invention has another advantage of being softer.

In one embodiment, the surgical thread has a tensile strength of 2.4 N to 100 N. Preferably, the tensile strength of the surgical thread is 2.5 N to 40 N. Specifically, when the modified cross-section fiber comprises polydioxanone (PDO), the tensile strength of the surgical thread is 5 N to 37 N; when the modified cross-section fiber comprises poly(L-lactide-co-caprolactone) (PLC), the tensile strength of the surgical thread is 2.5 N to 21 N; and/or when the modified cross-section fiber comprises poly(glycolide-co-L-lactide) (PGL), the tensile strength of the surgical thread is 4 N to 35 N.

The tensile strength is obtained according to the test method of USP<881> tensile strength. Specifically, the present invention adopts a universal material testing machine, and a target thread with a length of about 300 mm is clamped at its two ends by two clamps of the universal material testing machine. The distance between the two clamps is 150 mm, and the tensile strength of the target thread is measured at a tensile speed of 300 mm/min. Preferably, the universal material testing machine is purchased from MTS (US). More preferably, the specification of the target thread is that: (1) the fiber outer diameter of the target thread is 0.300 mm to 0.349 mm; (2) the amount of twist of the target thread is 450 TPM to 550 TPM (twist per meter); and (3) the target thread is twisted from a single strand of the modified cross-section fiber. Further preferably, the cross section of the single strand of the modified cross-section fiber is in a cross shape.

In one embodiment, the surgical thread has an elongation rate of 10% to 150%. Preferably, the elongation rate of the surgical thread is 40% to 61%. Specifically, when the modified cross-section fiber comprises polydioxanone (PDO), the surgical thread has an elongation rate of 41% to 48%; when the modified cross-section fiber comprises poly(L-lactide-co-caprolactone) (PLC), the surgical thread has an elongation rate of 56% to 60%; and/or when the modified cross-section fiber comprises poly(glycolide-co-L-lactide) (PGL), the surgical thread has an elongation rate of 48% to 54%.

The elongation rate indicates that based on the original length of the target thread, the percentage of the length of the elongation of the target thread upon broken by tension, wherein "the length of the elongation" is the length obtained by that the total length of the target thread after the elongation minus the original length of the target thread. Preferably, the elongation rate is obtained according to the test method of USP<881> tensile strength and is measured with the tensile strength simultaneously. More preferably, the specification of the target thread is that: (1) the fiber outer diameter of the target thread is 0.300 mm to 0.349 mm; (2) the amount of twist of the target thread is 450 TPM to 550 TPM (twist per meter); and (3) the target thread is twisted from a single strand of the modified cross-section fiber. Further preferably, the cross section of the single strand of the modified cross-section fiber is in a cross shape.

According to the present invention, the combination of the tensile strength and the elongation rate within the aforementioned specific range adopted by the surgical thread of the present invention can improve the softness of the surgical thread, thereby increasing the popularity in clinical applications.

In one embodiment, the degradation time of the surgical thread of the present invention is 1 month to 3 years. Specifically, the degradation time for poly(glycolide-co-L-lactide) (PGL) is about 1 month to 2 months; the degradation time for polydioxanone (PDO) is about 6 months; the degradation time for poly(L-lactide-co-caprolactone) (PLC) is about 12 months to 18 months; and the degradation time for poly(L-lactide) (PLLA) is about 2 years to 3 years.

The present invention further provides a cosmetic use of the surgical thread of the present invention, comprising providing the surgical thread to a subject in need thereof, wherein the surgical thread is embedded within a face of the subject.

Preferably, the cosmetic use comprises thread lifting.

According to the present invention, embedding the surgical thread within the face modifies the appearance of the face, and the cosmetic use of the surgical thread is non-therapeutic.

The present invention further provides a cosmetic treatment, comprising providing the surgical thread of the present invention to a subject in need thereof, wherein the surgical thread is embedded within a face of the subject.

Preferably, the surgical thread is implanted in a subcutaneous fat layer or a superficial muscular aponeurotic system (SMAS) layer of the face. More preferably, the efficacy for embedding the surgical thread within the face comprises reducing nasolabial folds or smile lines.

According to the present invention, embedding the surgical thread within the face has the efficacy of facial lifting so as to reduce nasolabial folds or smile lines.

The present invention further provides a manufacturing method for the surgical thread, comprising:

(1) a melt spinning step: melting a biodegradable material to obtain a thermoformed fiber by hot extrusion via a modified cross-section outlet, wherein the hot extrusion is processed at a temperature of 115° C. to 250° C.;
cooling the thermoformed fiber to obtain a cooled fiber; and
thermally drawing the cooled fiber to obtain a modified cross-section fiber; and
(2) a twisting step: twisting the modified cross-section fiber lengthwise and further carrying out heat setting to obtain a semi-finished product; and
cooling the semi-finished product to obtain the surgical thread.

The manufacturing method of the present invention comprises the advantages as follows: (1) adjusting the shape of the cross section of the modified cross-section fiber by means of the modified cross-section outlet to effectively control the density and coefficient of kinetic friction of the modified cross-section fiber; (2) effectively controlling the tensile strength, the elongation rate, the softness and fiber diameters of the surgical thread by means of thermally drawing the cooled fiber; and (3) enhancing the coefficient of kinetic friction of the surgical thread by means of the twisting step, so as to enhance the adhering capacity of the surgical thread, thereby enabling the surgical thread to stay in the tissue for a longer period.

Specifically, in the (1) melt spinning step, when the biodegradable material comprises polydioxanone (PDO), the temperature of the hot extrusion is from 180° C. to 230° C. Preferably, the temperature of the hot extrusion is from 200° C. to 210° C. More preferably, the temperature of the hot extrusion is from 204° C. to 206° C.

In the (1) melt spinning step, when the biodegradable material comprises poly(L-lactide-co-caprolactone) (PLC), the temperature of the hot extrusion is from 115° C. to 150° C. Preferably, the temperature of the hot extrusion is from 120° C. to 130° C. More preferably, the temperature of the hot extrusion is from 124° C. to 126° C.

In the (1) melt spinning step, when the biodegradable material comprises poly(glycolide-co-L-lactide) (PGL), the temperature of the hot extrusion is from 180° C. to 230° C. Preferably, the temperature of the hot extrusion is from 205° C. to 215° C. More preferably, the temperature of the hot extrusion is from 207° C. to 209° C.

In the (1) melt spinning step, when the biodegradable material comprises poly(L-lactide) (PLLA), the temperature of the hot extrusion is from 180° C. to 250° C. Preferably, the temperature of the hot extrusion is from 200° C. to 210° C. More preferably, the temperature of the hot extrusion is from 204° C. to 206° C.

In one embodiment, in the (1) melt spinning step, the temperature of the cooling is from 4° C. to 35° C. Preferably, the temperature of the cooling is from 15° C. to 25° C. More preferably, the temperature of the cooling is from 19° C. to 21° C.

In one embodiment, the melt spinning step adopts a melt spinning machine. In the (1) melt spinning step, the rotation speed of an extruder screw of the melt spinning machine is 2 rpm to 100 rpm; the winding speed for the cooled fiber is 2 m/min to 200 m/min; and/or the spinning length for the cooled fiber is 30 cm to 300 cm.

Preferably, the rotation speed of the extruder screw of the melt spinning machine is 10 rpm to 20 rpm; the winding speed for the cooled fiber is 10 m/min to 60 m/min; and/or the spinning length for the cooled fiber is 50 cm to 150 cm. More preferably, the rotation speed of the extruder screw of the melt spinning machine is 14 rpm to 16 rpm; the winding speed for the cooled fiber is 22 m/min to 28 m/min; and/or the spinning length for the cooled fiber is 70 cm to 90 cm.

In one embodiment, in the (1) melt spinning step, the temperature of the thermal drawing is 26° C. to 150° C.; and/or the amplification ratio of the thermal drawing is 2 times to 15 times.

Specifically, in the (1) melt spinning step, when the biodegradable material comprises polydioxanone (PDO), the temperature of the thermal drawing is 60° C. to 130° C., and/or the amplification ratio of the thermal drawing is 2 times to 15 times. Preferably, the temperature of the thermal drawing is 80° C. to 100° C., and/or the amplification ratio of the thermal drawing is 5 times to 10 times. More preferably, the temperature of the thermal drawing is 89° C. to 91° C., and/or the amplification ratio of the thermal drawing is 5 times to 7 times.

In the (1) melt spinning step, when the biodegradable material comprises poly(L-lactide-co-caprolactone) (PLC), the temperature of the thermal drawing is 26° C. to 100° C., and/or the amplification ratio of the thermal drawing is 2 times to 15 times. Preferably, the temperature of the thermal drawing is 40° C. to 80° C., and/or the amplification ratio of the thermal drawing is 5 times to 10 times. More preferably, the temperature of the thermal drawing is 49° C. to 51° C., and/or the amplification ratio of the thermal drawing is 6 times to 8 times.

In the (1) melt spinning step, when the biodegradable material comprises poly(glycolide-co-L-lactide) (PGL), the temperature of the thermal drawing is 50° C. to 120° C., and/or the amplification ratio of the thermal drawing is 2 times to 15 times. Preferably, the temperature of the thermal drawing is 60° C. to 90° C., and/or the amplification ratio of the thermal drawing is 4 times to 10 times. More preferably, the temperature of the thermal drawing is 79° C. to 81° C., and/or the amplification ratio of the thermal drawing is 5 times to 7 times.

In the (1) melt spinning step, when the biodegradable material comprises poly(L-lactide) (PLLA), the temperature of the thermal drawing is 70° C. to 150° C., and/or the amplification ratio of the thermal drawing is 2 times to 15 times. Preferably, the temperature of the thermal drawing is 80° C. to 120° C., and/or the amplification ratio of the thermal drawing is 4 times to 10 times. More preferably, the temperature of the thermal drawing is 99° C. to 101° C., and/or the amplification ratio of the thermal drawing is 7 times to 9 times.

In one embodiment, in the (1) melt spinning step, the winding speed for the modified cross-section fiber is 2 m/min to 100 m/min. Preferably, the winding speed for the modified cross-section fiber is 5 m/min to 30 m/min. More preferably, the winding speed for the modified cross-section fiber is 9 m/min to 11 m/min.

In one embodiment, in the (2) twisting step, the temperature of the heat setting for the modified cross-section fiber is the same as that of the thermal drawing in the (1) melt spinning step.

In one embodiment, in the (2) twisting step, the time of the heat setting for the modified cross-section fiber is 1 second to 120 seconds. Preferably, the time of the heat setting for the modified cross-section fiber is 3 seconds to 60 seconds. More preferably, the time of the heat setting for the modified cross-section fiber is 4 seconds to 6 seconds.

In one embodiment, in the (2) twisting step, the temperature of the cooling for the modified cross-section fiber is 4° C. to 30° C., and/or the time of the cooling for the modified cross-section fiber is 1 second to 120 seconds. Preferably, the temperature of the cooling for the modified cross-section fiber is 4° C. to 25° C., and/or the time of the cooling for the modified cross-section fiber is 5 seconds to 60 seconds. More preferably, the temperature of the cooling for the modified cross-section fiber is 19° C. to 21° C., and/or the time of the cooling for the modified cross-section fiber is 9 seconds to 11 seconds.

To sum up, the surgical thread of the present invention has the advantages as follows: (1) good coefficient of kinetic friction, tensile strength and the elongation rate; (2) reducing the weight burden on the face of the patients after the implantation of the surgical thread; (3) good softness; (4) promotion of collagen formation; and (5) good safety, comprising no inflammatory potential, no cytotoxicity, no pyrogen, no acute systemic toxicity and no intradermal irritation potential, thereby being suitable for embedding in the face. Further, the manufacturing method for the surgical thread of the present invention can effectively adjust the coefficient of kinetic friction of the surgical thread, tensile strength, the elongation rate and the softness.

DETAILED DESCRIPTION OF THE PREFERRED EMBODIMENTS

Figure 1A:
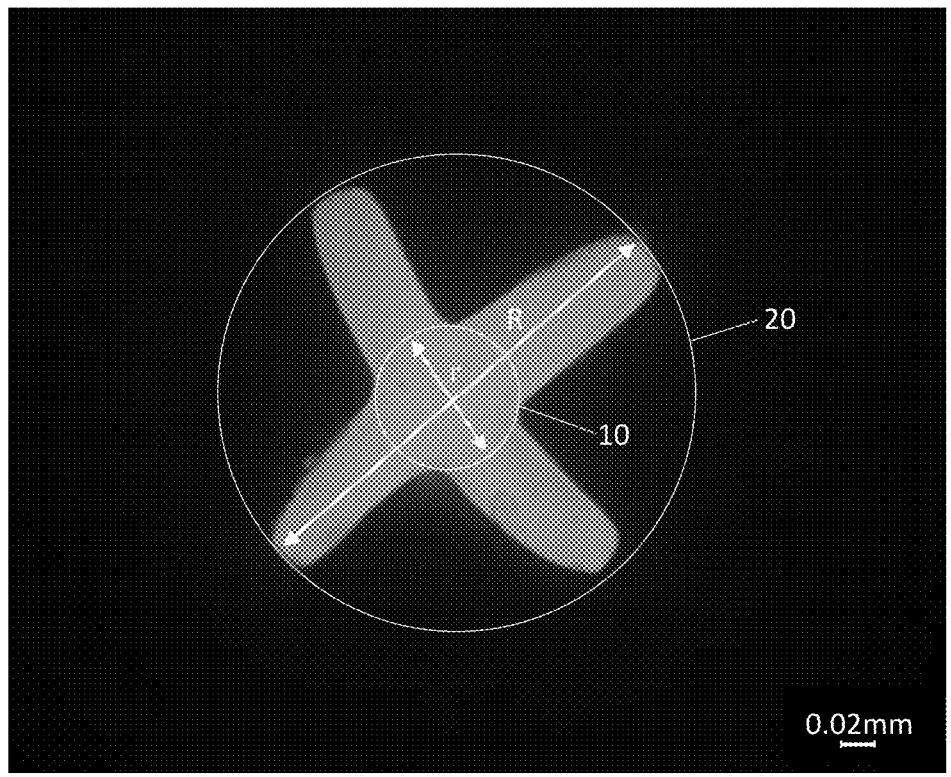
FIGS. 1A to 1C are photos of the modified cross-section fiber with cross section thereof in different shapes.

The present invention is further explained through the following embodiments. A person having ordinary skill in the art can easily understand the advantages and efficacies achieved by the present invention. The present invention should not be limited to the contents of the embodiments. A person having ordinary skill in the art can make some improvement or modifications which are not departing from the spirit and scope of the present invention to practice or apply the content of the present invention.

(1) Examples 1-1 to 4-1: The Surgical Thread

Each example adopted a small melt spinning machine (Xplore®) for carrying out (1) a melt spinning step: melting a biodegradable material to obtain a thermoformed fiber by hot extrusion via a modified cross-section outlet, cooling the thermoformed fiber to obtain a cooled fiber; and thermally drawing the cooled fiber to obtain a modified cross-section fiber, which were the modified cross-section (cross-shaped) fibers 1-1 to 4-1; and (2) a twisting step: twisting the modified cross-section fiber (the modified cross-section (cross-shaped) fibers 1-1 to 4-1) lengthwise and further carrying out heat setting to obtain a semi-finished product; and cooling the semi-finished product to obtain the surgical thread, which were Examples 1-1 to 4-1; wherein the biodegradable material, the temperature of the hot extrusion (abbreviated as "extruder temperature" hereinafter), the rotation speed of the extruder screw, the temperature of the cooling for the thermoformed fiber, the winding speed and the spinning length for the cooled fiber, the temperature of the thermal drawing (abbreviated as "thermal drawing temperature" hereinafter), the amplification ratio of the thermal drawing (abbreviated as "draw ratio" hereinafter), the winding speed for the modified cross-section fiber, the amount of twist, the temperature of the heat setting, the time of the heat setting, the temperature of the cooling for the semi-finished product and the time of the cooling in each example were shown in Table 1.

Further, for the biodegradable material of poly(L-lactide-co-caprolactone) (PLC), based on the total moles of L-lactide and caprolactone, L-lactide was in an amount of 65 molar percent to 75 molar percent, and caprolactone was in an amount of 25 molar percent to 35 molar percent; and for the biodegradable material of poly(glycolide-co-L-lactide) (PGL), based on the total moles of glycolide and L-lactide, glycolide was in an amount of 87 molar percent to 93 molar percent, and L-lactide was in an amount of 7 molar percent to 13 molar percent. Finally, the modified cross-section (cross-shaped) fibers 1-1 to 4-1 and Examples 1-1 to 4-1 each had a fiber outer diameter of 0.328 mm, and a fiber inner diameter of 0.1017 mm.

TABLE 1

The name of the biodegradable material and the inherent viscosity thereof, the extruder temperature, the rotation speed of the extruder screw, the temperature of the cooling for the thermoformed fiber, the winding speed and the spinning length for the cooled fiber, the thermal drawing temperature, the draw ratio, the winding speed for the modified cross-section fiber, the amount of twist, the temperature of the heat setting, the time of the heat setting, the temperature of the cooling for the semi-finished product and the time of the cooling for Examples 1-1 to 4-1

| | | Example 1-1 | Example 2-1 | Example 3-1 | Example 4-1 |
|---|---|---|---|---|---|
| The biodegradable material | Name | PDO | PLC | PGL | PLLA |
| | The inherent viscosity (dL/g) | 1.85 | 1.52 | 1.15 | 3.82 |
| The extruder temperature (° C.) | | 205 | 125 | 208 | 205 |
| The rotation speed of the extruder screw (RPM) | | 15 | 15 | 15 | 15 |
| The temperature of the cooling for the thermoformed fiber (° C.) | | 20 | 20 | 20 | 20 |
| The cooled fiber | the winding speed (m/min) | 25 | 25 | 25 | 25 |
| | the spinning length (cm) | 80 | 80 | 80 | 80 |
| The thermal drawing temperature (° C.) | | 90 | 50 | 80 | 100 |
| The draw ratio (times) | | 6 | 7 | 6 | 8 |
| The winding speed for the modified cross-section fiber (m/min) | | 10 | 10 | 10 | 10 |
| The amount of twist (TPM) | | 500 | 500 | 500 | 500 |
| The temperature of the heat setting (° C.) | | 90 | 50 | 80 | 100 |
| The time of the heat setting (second) | | 5 | 5 | 5 | 5 |
| The temperature of the cooling for the semi-finished product (° C.) | | 20 | 20 | 20 | 20 |
| The time of the cooling (second) | | 10 | 10 | 10 | 10 |

(2) The Analysis for the Fiber Inner Diameter and the Fiber Outer Diameter of the Modified Cross-Section Fiber This analysis comprised three fibers of different sizes: two modified cross-section (cross-shaped) fibers 1-2 and 1-3 (untwisted) and one modified cross-section (Y-shaped) fibers 5-1 (untwisted). By measuring the target fiber in the photo, the fiber inner diameter and the fiber outer diameter thereof were obtained, and the results were shown in Table 2; wherein (1) the manufacturing methods of the modified cross-section (cross-shaped) fibers 1-2 and 1-3 were similar to that of the modified cross-section (cross-shaped) fiber 1-1, and the difference thereof was the lengths of the fiber outer diameter and the fiber inner diameter; (2) the manufacturing method of the modified cross-section (Y-shaped) fibers 5-1 was similar to that of the modified cross-section (cross-shaped) fiber 1-1, and the differences thereof were: (A) the shape of the modified cross-section outlet that the modified cross-section (Y-shaped) fiber 5-1 adopted a Y-shaped shape outlet, and (B) the lengths of the fiber outer diameter and the fiber inner diameter.

TABLE 2 the measurement results of the fiber inner diameter, the fiber outer diameter and the ratio of the fiber inner diameter to the fiber outer diameter (abbreviated as "the fiber inner/outer ratio" hereinafter) of the modified cross-section fibers

Figure 1B:
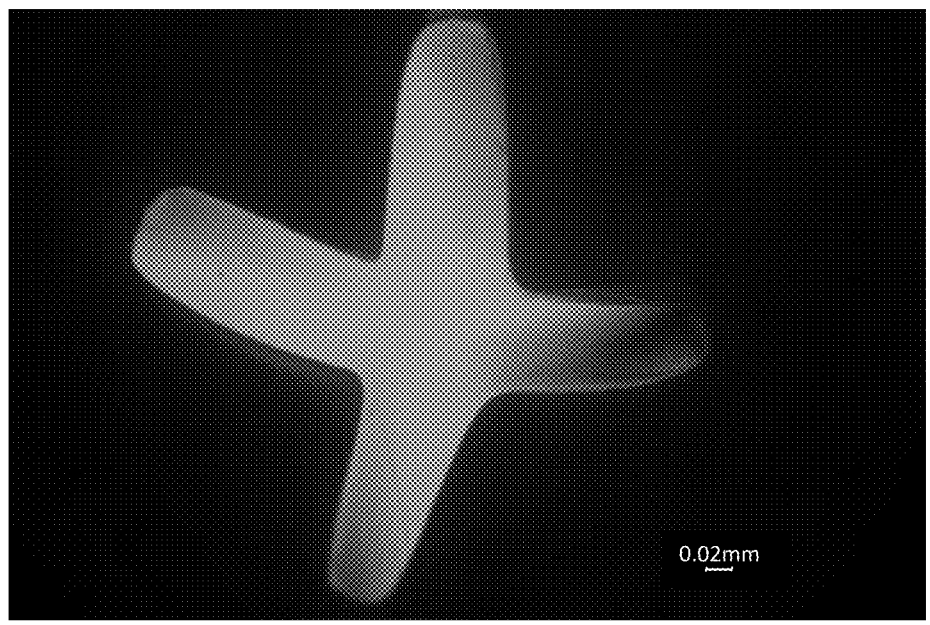
Figure 1C:
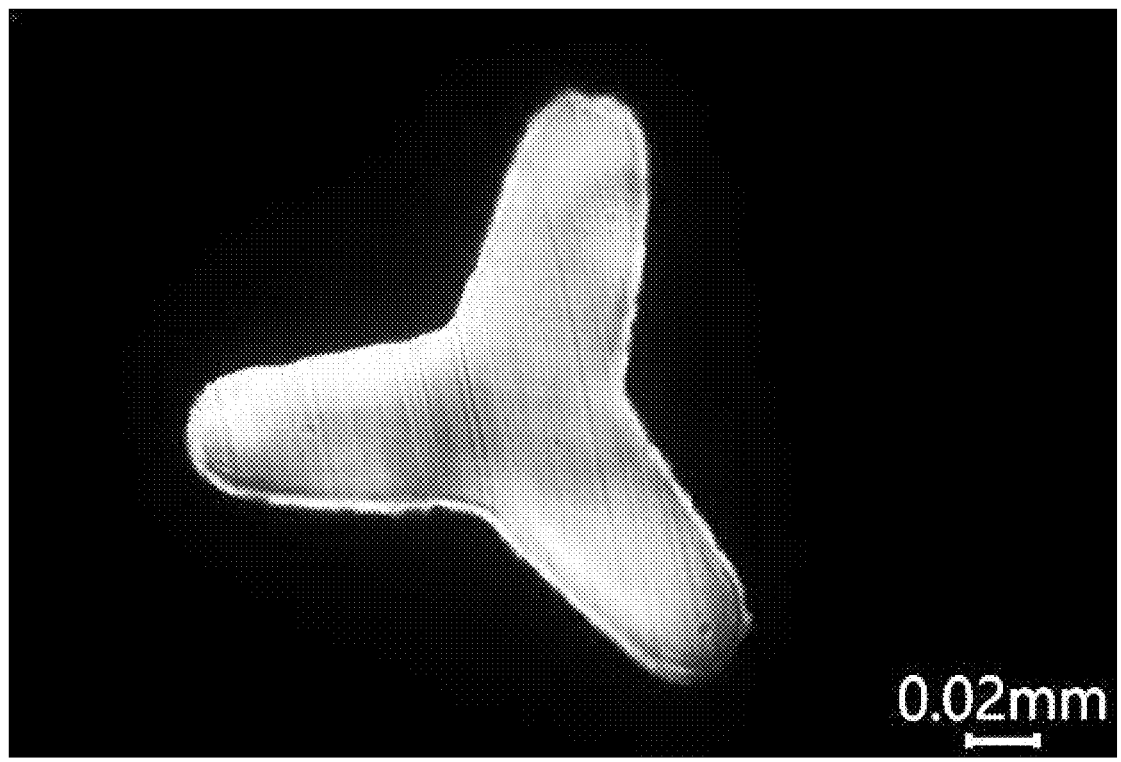

|  | The modified cross-section (cross-shaped) fibers (untwisted) |  | The modified cross-section (Y-shaped) fibers (untwisted) |
| --- | --- | --- | --- |
|  | 1-2 | 1-3 | 5-1 |
| The fiber inner diameter (mm) | 0.0921 | 0.1481 | 0.0655 |
| The fiber outer diameter (mm) | 0.2929 | 0.4852 | 0.1940 |
| The fiber inner/outer ratio | 0.314 | 0.305 | 0.338 |
| The photo | FIG. 1A | FIG. 1B | FIG. 1C |

As shown in FIG. 1A, the modified cross-section (cross-shaped) fibers 1-2 had a central region, which was the first imaginary circle 10, and four arms; wherein the first imaginary circle 10 had the longest diameter r, which was 0.0921 mm. The second imaginary circle 20 was depicted according to the four arms, wherein the second imaginary circle 20 had the diameter R, which was 0.2929 mm.

As shown in Table 2, the modified cross-section (cross-shaped) fibers 1-2 and 1-3 (untwisted) and the modified cross-section (Y-shaped) fibers 5-1 (untwisted) had a similar fiber inner/outer ratio. Therefore, the modified cross-section fiber of the present invention can adopt different sizes of the fiber inner diameter and the fiber outer diameter, and different shapes of the cross section to achieve a similar fiber inner/outer ratio, facilitating the subsequent twisting process and reserving a space for additional additives and the cell adhesions in the tissue.

(2) The Surface Analysis of the Modified Cross-Section Fiber and the Circular Cross-Section Fiber This analysis comprised the circular cross-section fiber 1-1 (untwisted) and the modified cross-section (cross-shaped) fiber 1-1 (untwisted); wherein the circular cross-section fiber 1-1 and the modified cross-section (cross-shaped) fibers 1-1 had the same fiber outer diameter, and the manufacturing method of the circular cross-section fiber 1-1 was similar to that of the modified cross-section (cross-shaped) fibers 1-1, wherein the difference was that the circular cross-section fiber 1-1 adopted a circular outlet.

By measuring the perimeters of the cross sections of both fibers, the surfaces of both fibers were calculated and compared, wherein the perimeter of the circular cross-section fiber 1-1 served as the basis, which was indicated as 1, the results were shown in Table 3.

TABLE 3 the perimeter ratios of the circular cross-section fiber 1-1 and the modified cross-section (cross-shaped) fibers 1-1

|  | The circular cross-section fiber 1-1 (untwisted) | The modified cross-section (cross-shaped) fibers 1-1 (untwisted) |
| --- | --- | --- |
| The perimeter ratio | 1 | 1.2113 |

As shown in Table 3, the perimeter of the modified cross-section (cross-shaped) fibers 1-1 was about 1.2 times larger than that of the circular cross-section fiber 1-1. Therefore, if both fibers had the same total length, the surface of the modified cross-section (cross-shaped) fibers 1-1 would also be about 1.2 times larger than that of the circular cross-section fiber 1-1. In other words, when both fibers had the same fiber outer diameter, the modified cross-section (cross-shaped) fiber 1-1 of the present invention indeed increased the surface per unit length, thereby increasing the space for the cell adhesions in the tissue.

(3) Analysis of the Twisted States of the Modified Cross-Section Fiber

This analysis comprised the modified cross-section (cross-shaped) fiber 6-1 (untwisted), and twisted modified cross-section (cross-shaped) fibers 6-1 to 6-5, which were Examples 6-1 to 6-5, and the structural differences were shown in Table 4; wherein the manufacturing method of the modified cross-section (cross-shaped) fiber 6-1 was similar to that of the modified cross-section (cross-shaped) fiber 1-1, wherein the difference was that the modified cross-section (cross-shaped) fiber 6-1 (untwisted) was further added with 0.1% (w/w) dye of D&C VIOLET NO. 2 approved by FDA; and the manufacturing methods of Examples 6-1 to 6-5 were similar to that of the modified cross-section (cross-shaped) fiber 1-1, wherein the differences were that (A) Examples 6-1 to 6-5 were further added with 0.1% (w/w) dye of D&C VIOLET NO. 2, and (B) Examples 6-1 to 6-5 had different twisted states. For clarification, D&C VIOLET NO. 2 provided colors to said fiber, thereby making said fiber more visible to facilitate carrying out the experiment, and had no impact on the analysis results.

TABLE 4 the structural differences of the modified cross-section (cross-shaped) fibers 6-1 (untwisted) and Examples 6-1 to 6-5

Figure 2A:
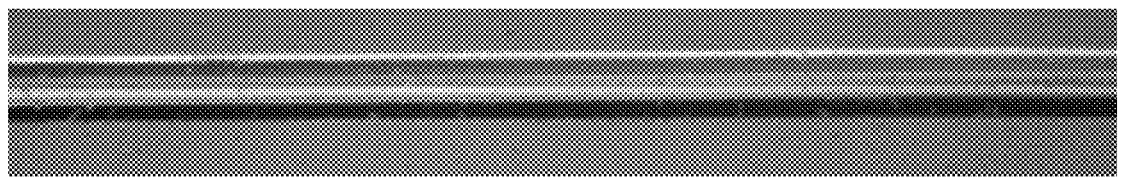
FIG. 2A is the photo of the modified cross-section (cross-shaped) fiber 6-1 (untwisted)
Figure 2B:
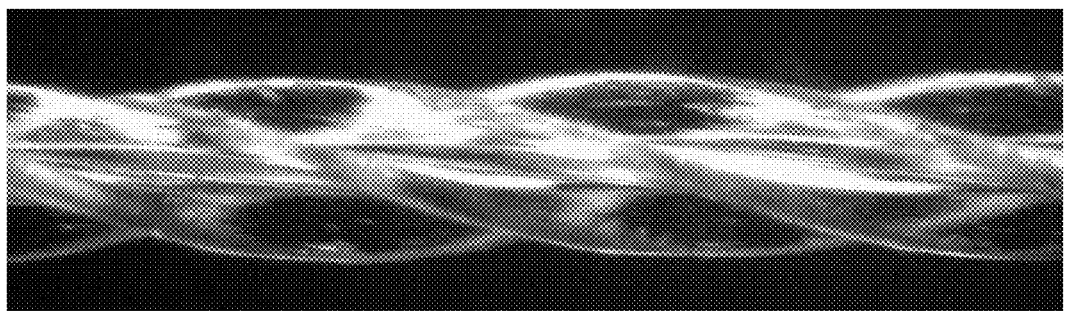
FIGS. 2B to 2D are the photos of the modified cross-section (cross-shaped) fibers 6-1 to 6-3 (Examples 6-1 to 6-3) in different twisted states.
Figure 2C:
Figure 2D:
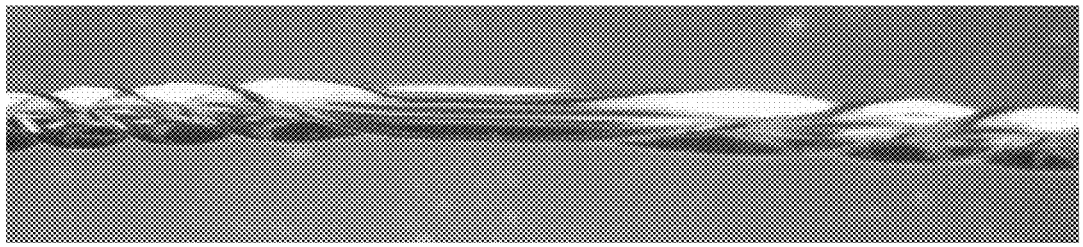

| Group | The twist direction | The amount of twist (TPM) | The photo |
| --- | --- | --- | --- |
| The modified cross-section (cross-shaped) fiber 6-1 (untwisted) | N/A | N/A | FIG. 2A |
| Example 6-1 | Z-twist (clockwise) | 500 | FIG. 2B |
| Example 6-2 | S-twist (counterclockwise) | 500 | FIG. 2C |
| Example 6-3 | Z-S twist | 500 for each | FIG. 2D |
| Example 6-4 | Z-S-Z twist | 500 for each | N/A |
| Example 6-5 | S-Z-S twist | 500 for each | N/A |

As shown in FIG. 2A, the modified cross-section (cross-shaped) fiber 6-1 (untwisted) was not in a twisted state. As shown in FIG. 2B and FIG. 2C, Examples 6-1 and 6-2 were both in a twisted state, and the twisted states thereof were in opposite directions. As shown in FIG. 2D, Example 6-3 comprised the twisted states in opposite directions at the same fiber simultaneously.

Figure 2E:
FIG. 2E is the schematic diagram of Examples 6-1 to 6-5 in different twisted states.

Further, the schematic diagram of the structural differences of Examples 6-1 to 6-5 was shown in FIG. 2E; wherein Example 6-1 comprised three segments (from left to right): the segment in an untwisted state with the length of 1 cm, the segment with a Z-twist with the length of 14 cm, and the segment in an untwisted state with the length of 5 cm; Example 6-2 comprised three segments (from left to right): the segment in an untwisted state with the length of 1 cm, the segment with an S-twist with the length of 14 cm, and the segment in an untwisted state with the length of 5 cm; Example 6-3 comprised five segments (from left to right): the segment in an untwisted state with the length of 1 cm, the segment with a Z-twist with the length of 6 cm, the segment in an untwisted state with the length of 2 cm, the segment with an S-twist with the length of 6 cm, and the segment in an untwisted state with the length of 5 cm; Example 6-4 comprised seven segments (from left to right): the segment in an untwisted state, the segment with a Z-twist, the segment in an untwisted state, the segment with an S-twist, the segment in an untwisted state, the segment with a Z-twist and the segment in an untwisted state; and Example 6-5 comprised seven segments (from left to right): the segment in an untwisted state, the segment with a S-twist, the segment in an untwisted state, the segment with a Z-twist, the segment in an untwisted state, the segment with an S-twist and the segment in an untwisted state.

(4) Analysis of the Coefficient of Kinetic Friction of the Surgical Threads

This analysis comprised the circular cross-section fibers 1-1 to 3-1 and Examples 1-1 to 3-1; wherein the biodegradable materials of the circular cross-section fibers 1-1 to 3-1 corresponded to those of Examples 1-1 to 3-1 one by one, which were polydioxanone (PDO), poly(L-lactide-co-caprolactone) (PLC) and poly(glycolide-co-L-lactide) (PGL) in order.

Further, the manufacturing methods of the circular cross-section fibers 1-1 to 3-1 were similar to those of Examples 1-1 to 3-1 one by one, wherein the differences were that: (A) the circular cross-section fibers 1-1 to 3-1 adopted a circular outlet; (B) the circular cross-section fibers 1-1 to 3-1 were not in a twisted state, as the circular cross-section fiber cannot be twisted to form a twisted state.

The coefficient of kinetic frictions of the circular cross-section fibers 1-1 to 3-1 and Examples 1-1 to 3-1 were measured according to the international standard of ASTM D3108/D3108M-13 (Standard Test Method For Coefficient Of Friction, Yarn To Solid Material). By using the portable mechanical yarn friction tester purchased from Standard International Group (HK) Limited, the coefficient of kinetic frictions of the circular cross-section fibers 1-1 to 3-1 and Examples 1-1 to 3-1 were measured against the friction plate (a metal wheel) at a speed of 5 m/min.

Further, the increase rate of the coefficient of kinetic frictions were respectively calculated according to the formula as follows: the increase rate of the coefficient of kinetic frictions=(the coefficient of kinetic friction of the Example–the coefficient of kinetic friction of the corresponding circular cross-section fiber)/the coefficient of kinetic friction of the corresponding circular cross-section fiber*100%. The results were shown in Table 5.

TABLE 5 the coefficient of kinetic friction and the increase rate thereof of the circular cross-section fibers 1-1 to 3-1 and Examples 1-1 to 3-1

| Group number | The coefficient of kinetic friction | | The increase rate of the coefficient of kinetic friction (%) |
| --- | --- | --- | --- |
| | The circular cross-section fiber | Example | |
| 1-1 | 0.34 | 0.43 | 26.5 |
| 2-1 | 0.34 | 0.42 | 23.5 |
| 3-1 | 0.28 | 0.36 | 28.6 |

As shown in Table 5, when the biodegradable materials were chosen among PDO, PLC and PGL, the corresponding increase rates of the coefficient of kinetic friction were different. Further, Example 3-1, which adopted PGL, had the highest increase rate of the coefficient of kinetic friction of 28.6%. Nonetheless, as Example 3-1 had the coefficient of kinetic friction of 0.36, which was significantly lower than that of Example 1-1 of 0.43, PDO was the better choice for the biodegradable material.

(5) Analysis of the Tensile Strength, the Elongation Rate and the Density of the Surgical Threads This analysis comprised as follows:
A. the circular cross-section fibers 1-1 to 3-1.
B. Example 1-1, Example 1-2, and Examples 1-4 to 1-6, wherein all the biodegradable materials thereof were PDO, and the manufacturing methods of Example 1-2, and Examples 1-4 to 1-6 were similar to that of Example 1-1, wherein the difference was that both the fiber inner diameters and the fiber outer diameters of Example 1-1, Example 1-2, and Examples 1-4 to 1-6 were different.
C. Examples 2-1 to 2-4, wherein all the biodegradable materials thereof were PLC, and the manufacturing methods of Examples 2-2 to 2-4 were similar to that of Example 2-1, wherein the difference was that both the fiber inner diameters and the fiber outer diameters of Examples 2-1 to 2-4 were different.
D. Examples 3-1 to 3-5, wherein all the biodegradable materials thereof were PGL, and the manufacturing methods of Examples 3-2 to 3-5 were similar to that of Example 3-1, wherein the difference was that both the fiber inner diameters and the fiber outer diameters of Examples 3-1 to 3-5 were different.

Finally, Example 1-1, Example 2-1 and Example 3-1, and the circular cross-section fibers 1-1 to 3-1 had the same fiber outer diameter.

I. The Analysis of the Tensile Strength and the Elongation Rate

This analysis followed the standard of USP<881> tensile strength, and adopted the universal material testing machine purchased from MTS (US) to measure the tensile strength and the elongation rate simultaneously; wherein the thread of each group with the length of about 300 mm was clamped at its two ends by two clamps of the universal material testing machine. The distance between the two clamps was 150 mm, and the tensile strength and the elongation rate were measured simultaneously at a tensile speed of 300 mm/min.

II. The Analysis of the Density

The weight of the thread of each group with a length of 300 mm was measured by a precision balance (brand:

Mettler Toledo, model: Balance XPR204S) to obtain the weight per unit length of the thread of each group. Further, the fiber outer diameter of the thread of each group was measured by a thickness gauge for calculating the density of the thread of each group. Finally, the inner diameter of the thread of each group was measured by a microscope. The results were shown in Table 6.

Besides, the specification in <USP 861> is as follows:
A. 1:0.400 mm to 0.499 mm.
B. 0:0.350 mm to 0.399 mm.
C. 2-0:0.300 mm to 0.349 mm.
D. 3-0:0.200 mm to 0.249 mm.
E. 4-0:0.150 mm to 0.199 mm.
F. 5-0:0.100 mm to 0.149 mm.
G. 6-0:0.070 mm to 0.099 mm.
H. 7-0:0.050 mm to 0.069 mm.

For clarification, according to the standard of <USP 861>, 3-0 is 0.200 mm to 0.249 mm, not 0.200 mm to 0.299 mm. However, when the fiber outer diameter of the modified cross-section fiber is within 0.25 mm to 0.299 mm, such fiber outer diameter will still be classified as 3-0 in practice, as the mechanical strength thereof is inevitably weaker than that of the circular cross-section fiber with the same outer diameter.

TABLE 6 the tensile strength, the elongation rate and the density of the circular cross-section fibers 1-1 to 3-1, Example 1-1, Example 1-2, Examples 1-4 to 1-6, Examples 2-1 to 2-4 and Examples 3-1 to 3-5

| Group | <USP 861> | | The tensile strength (N) | The elongation rate (%) | The density (g/cm$^3$) |
|---|---|---|---|---|---|
| | The fiber outer diameter | The fiber inner diameter | | | |
| The circular cross-section fiber 1-1 | 2-0 | N/A | 30.45 ± 1.23 | 43.33 ± 2.38 | 1.256 |
| Example 1-1 | 2-0 | 5-0 | 16.32 ± 0.78 | 45.24 ± 3.63 | 0.608 |
| Example 1-2 | 3-0 | 6-0 | 9.77 ± 0.91 | 43.55 ± 4.01 | 0.608 |
| Example 1-4 | 1 | 4-0 | 36.12 ± 1.97 | 47.31 ± 4.11 | 0.606 |
| Example 1-5 | 0 | 5-0 | 23.15 ± 1.66 | 45.65 ± 3.98 | 0.607 |
| Example 1-6 | 4-0 | 7-0 | 5.67 ± 0.63 | 42.18 ± 3.28 | 0.612 |
| The circular cross-section fiber 2-1 | 2-0 | N/A | 28.32 ± 1.16 | 52.12 ± 2.45 | 1.198 |
| Example 2-1 | 2-0 | 5-0 | 10.78 ± 0.92 | 57.22 ± 4.26 | 0.578 |
| Example 2-2 | 0 | 5-0 | 20.15 ± 1.89 | 59.45 ± 4.71 | 0.572 |
| Example 2-3 | 3-0 | 6-0 | 7.02 ± 0.64 | 57.67 ± 4.02 | 0.581 |
| Example 2-4 | 4-0 | 7-0 | 3.03 ± 0.41 | 56.47 ± 4.19 | 0.583 |
| The circular cross-section fiber 3-1 | 2-0 | N/A | 29.87 ± 1.92 | 48.41 ± 2.92 | 1.432 |
| Example 3-1 | 2-0 | 5-0 | 14.32 ± 0.85 | 50.21 ± 3.85 | 0.618 |
| Example 3-2 | 1 | 4-0 | 33.92 ± 2.32 | 53.25 ± 3.32 | 0.616 |
| Example 3-3 | 0 | 5-0 | 22.15 ± 1.89 | 51.15 ± 3.89 | 0.617 |
| Example 3-4 | 3-0 | 6-0 | 8.88 ± 0.65 | 49.67 ± 2.85 | 0.619 |
| Example 3-5 | 4-0 | 7-0 | 4.84 ± 0.32 | 48.33 ± 2.77 | 0.621 |

From the comparison of the circular cross-section fiber 1-1 and Example 1-1, under the condition of the same fiber outer diameter, Example 1-1 had the tensile strength of 16.32 N, which was significantly lower than 30.45 N of the circular cross-section fiber 1-1; and Example 1-1 had the density of 0.608 g/cm$^3$, which was significantly lower than 1.256 g/cm$^3$ of the circular cross-section fiber 1-1. However, under the condition that the fiber "inner" diameter of the surgical thread of the present invention is the same as the fiber "outer" diameter, which is the diameter of the cross section of the circular shape, of the circular cross-section fiber, the surgical thread of the present invention is estimated to have a higher tensile strength than that of a circular cross-section fiber.

Further, from the comparison of Example 1-1, Example 2-1 and Example 3-1, under the condition that all groups had the same lengths of the fiber outer diameter and the same fiber inner diameter, Example 1-1, which adopted PDO, had the highest tensile strength of 16.32 N, which was higher than (1) 10.78 N of Example 2-1, which adopted PLC; and (2) 14.32 N of Example 3-1, which adopted PGL.

Further, Example 2-1, which adopted PLC, had the highest elongation rate of 57.22%; and Example 3-1, which adopted PGL, had the highest density of 0.618 g/cm$^3$.

(6) The Cell Adhesion Experiment for the Comparison of the Shape of the Cross Section of the Fibers This experiment comprised 4 groups: the circular cross-section fiber 6-1 (untwisted), the modified cross-section (cross-shaped) fiber 6-1 (untwisted), the circular cross-section fiber 7-1 (untwisted) and modified cross-section (cross-shaped) fiber 7-1 (untwisted).

A. the circular cross-section fiber 6-1 (untwisted) and the modified cross-section (cross-shaped) fiber 6-1 (untwisted); wherein (A1) the manufacturing method of the circular cross-section fiber 6-1 (untwisted) was similar to that of the modified cross-section (cross-shaped) fiber 1-1, and the differences were that: I. the circular cross-section fiber 6-1 (untwisted) adopted a circular outlet; and II. the circular cross-section fiber 6-1 (untwisted) was further added with 0.1% (w/w) dye of D&C VIOLET NO. 2; and (A2) the manufacturing method of the modified cross-section (cross-shaped) fiber 6-1 (untwisted) was similar to that of the modified cross-section (cross-shaped) fiber 1-1, and the difference was that the modified cross-section (cross-shaped) fibers 6-1 (untwisted) was further added with 0.1% (w/w) dye of D&C VIOLET NO. 2.

Further, both the circular cross-section fiber 6-1 (untwisted) and the modified cross-section (cross-shaped) fiber 6-1 (untwisted) had the same biodegradable material of PDO and the same fiber outer diameter; wherein the difference thereof was the shape of cross section of the fibers.

B. the circular cross-section fiber 7-1 (untwisted) and modified cross-section (cross-shaped) fiber 7-1 (untwisted); wherein (B1) the manufacturing method of the circular cross-section fiber 7-1 (untwisted) was similar to that of the modified cross-section (cross-shaped) fiber 2-1, and the differences were that: I. the circular cross-section fiber 7-1 (untwisted) adopted a circular outlet; and II. the circular cross-section fiber 7-1 (untwisted) was further added with 0.1% (w/w) dye of D&C VIOLET NO. 2; and (B2) the manufacturing method of the modified cross-section (cross-shaped) fibers 7-1 (untwisted) was similar to that of the modified cross-section (cross-shaped) fiber 2-1, and the difference was that the modified cross-section (cross-shaped) fibers 7-1 (untwisted) was further added with 0.1% (w/w) dye of D&C VIOLET NO. 2.

Further, both the circular cross-section fiber 7-1 (untwisted) and the modified cross-section (cross-shaped) fiber 7-1 (untwisted) had the same biodegradable material of PLC and the same fiber outer diameter; wherein the difference thereof was the shape of cross section of the fibers.

This experiment comprised the following steps:

The mouse fibroblasts (L929 cell line, 5×10$^4$ cells per well) were seeded into a 24-well culture plate for each group; wherein said each group was added with a respective one of said fibers, which all had the same fiber outer diameters, in an amount of 0.01 g, and cultured at 37° C. in α-MEM medium supplemented with 10% horse serum. For clarification, 0.01 g of said fiber can surround a single hole of the 24-well culture plate several times, and was long enough for analysis.

The fibers in each group were taken out after 1, 3, 5 and 7 days of culture, and analyzed by the MTS cell activity analysis kit, and the absorbance at 490 nm for each group was measured by a spectrophotometer to evaluate the cell proliferation of the mouse fibroblasts in each group. As the mouse fibroblasts nearly reached full confluence and nearly covered all the surface of said fiber after 5 days of culture, the absorbance at 490 nm for each group after the 5 days of culture was chosen for comparison; wherein the cell proliferation amount of the circular cross-section fiber 6-1 (untwisted) served as the basis and was indicated as 1 for the comparison with that of the modified cross-section (cross-shaped) fibers 6-1 (untwisted); and the cell proliferation amount of the circular cross-section fiber 7-1 (untwisted) served as the basis and was indicated as 1 for the comparison with that of the modified cross-section (cross-shaped) fibers 7-1 (untwisted). The results were shown in FIG. 3.

Figure 3:
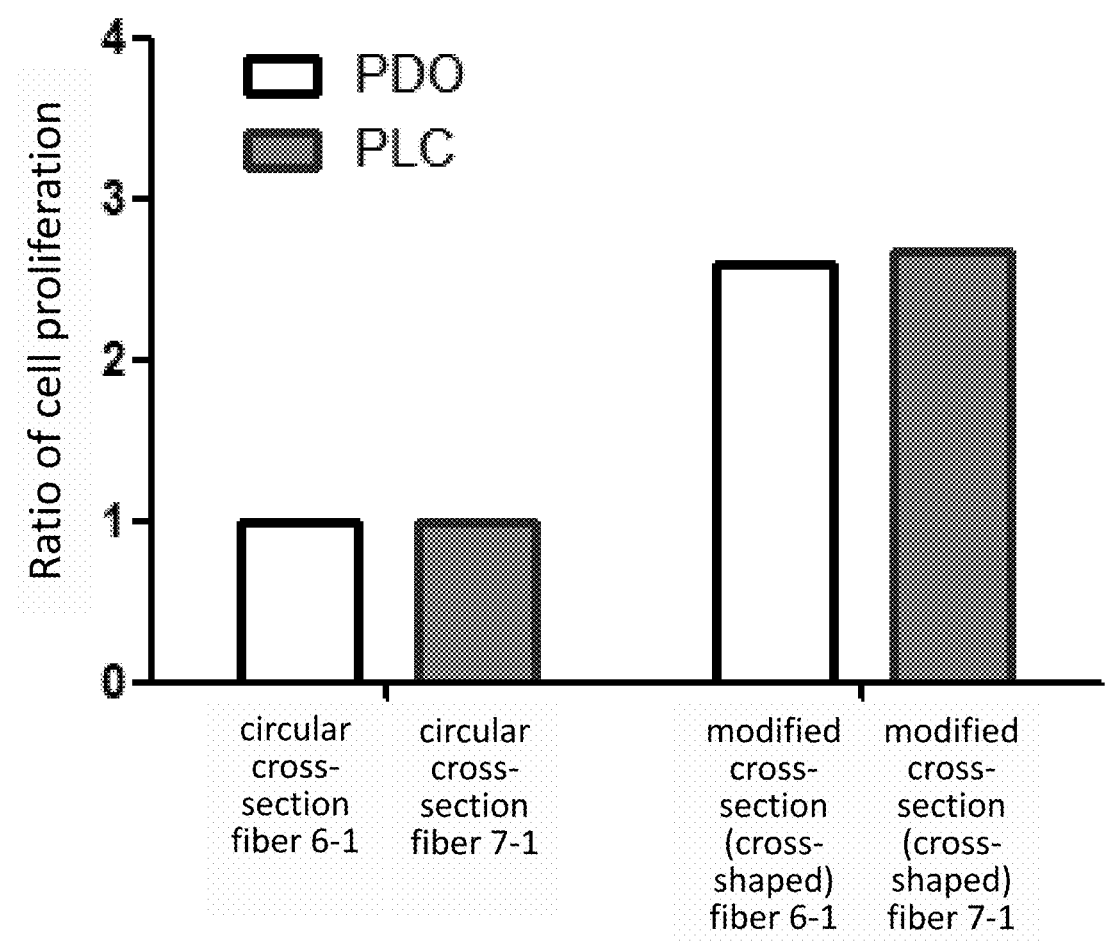
FIG. 3 is the bar chart of the cell proliferation ratio of the circular cross-section fibers 6-1 and 7-1, and the modified cross-section (cross-shaped) fibers 6-1 and 7-1.

As shown in FIG. 3, under the condition of the same biodegradable materials and the same fiber outer diameters, the cell proliferation amount of the modified cross-section (cross-shaped) fibers 6-1 (untwisted) was about 3 times higher than that of the circular cross-section fiber 6-1 (untwisted). Also, the cell proliferation amount of the modified cross-section (cross-shaped) fibers 7-1 (untwisted) was about 3 times higher than that of the circular cross-section fiber 7-1 (untwisted). Therefore, under the condition of the same fiber outer diameter, the modified cross-section fiber had better cell adhesion efficacy than the circular cross-section fiber, and had the efficacy to improve cell adhesion.

Further, while the surface of the modified cross-section (cross-shaped) fibers 6-1 (untwisted) was about 1.2 times larger than that of the circular cross-section fiber 6-1 (untwisted), and the cell proliferation amount of the modified cross-section (cross-shaped) fibers 6-1 was about 3 times higher than that of the circular cross-section fiber 6-1 (untwisted). Therefore, the modified cross-section fiber of the present invention can achieve unexpected efficacy of cell adhesion improvement.

(7) The Cell Adhesion Experiment for the Comparison of the Twisted/Untwisted State of the Fibers This experiment comprised 3 groups: the circular cross-section fiber 7-1 (untwisted), the modified cross-section (cross-shaped) fibers 7-1 (untwisted) 17 and the twisted modified cross-section (cross-shaped) fibers 7-1 (Example 7-1); wherein all said three fibers had the same biodegradable materials of PLC, and the same fiber outer diameter.

As mentioned above, the manufacturing method of the circular cross-section fiber 7-1 (untwisted) was similar to that of the modified cross-section (cross-shaped) fiber 2-1, and the differences were that: I. the circular cross-section fiber 7-1 (untwisted) adopted a circular outlet; and II. the circular cross-section fiber 7-1 (untwisted) was further added with 0.1% (w/w) dye of D&C VIOLET NO. 2.

As mentioned above, the manufacturing method of the modified cross-section (cross-shaped) fiber 7-1 (untwisted) was similar to that of the modified cross-section (cross-shaped) fiber 2-1, and the difference was that the modified cross-section (cross-shaped) fibers 7-1 (untwisted) was further added with 0.1% (w/w) dye of D&C VIOLET NO. 2.

The manufacturing method of the twisted modified cross-section (cross-shaped) fiber 7-1 (Example 7-1) was similar to that of Example 2-1, and the difference was that Example 7-1 was further added with 0.1% (w/w) dye of D&C VIOLET NO. 2.

This experiment comprised the same step as that in (6) the cell adhesion experiment for the comparison of the shape of the cross section of the fibers; wherein the cell proliferation amount of the circular cross-section fiber 7-1 (untwisted) served as the basis and was indicated as 1 for the comparison of the cell proliferation amount. The results were shown in FIG. 4.

Figure 4:
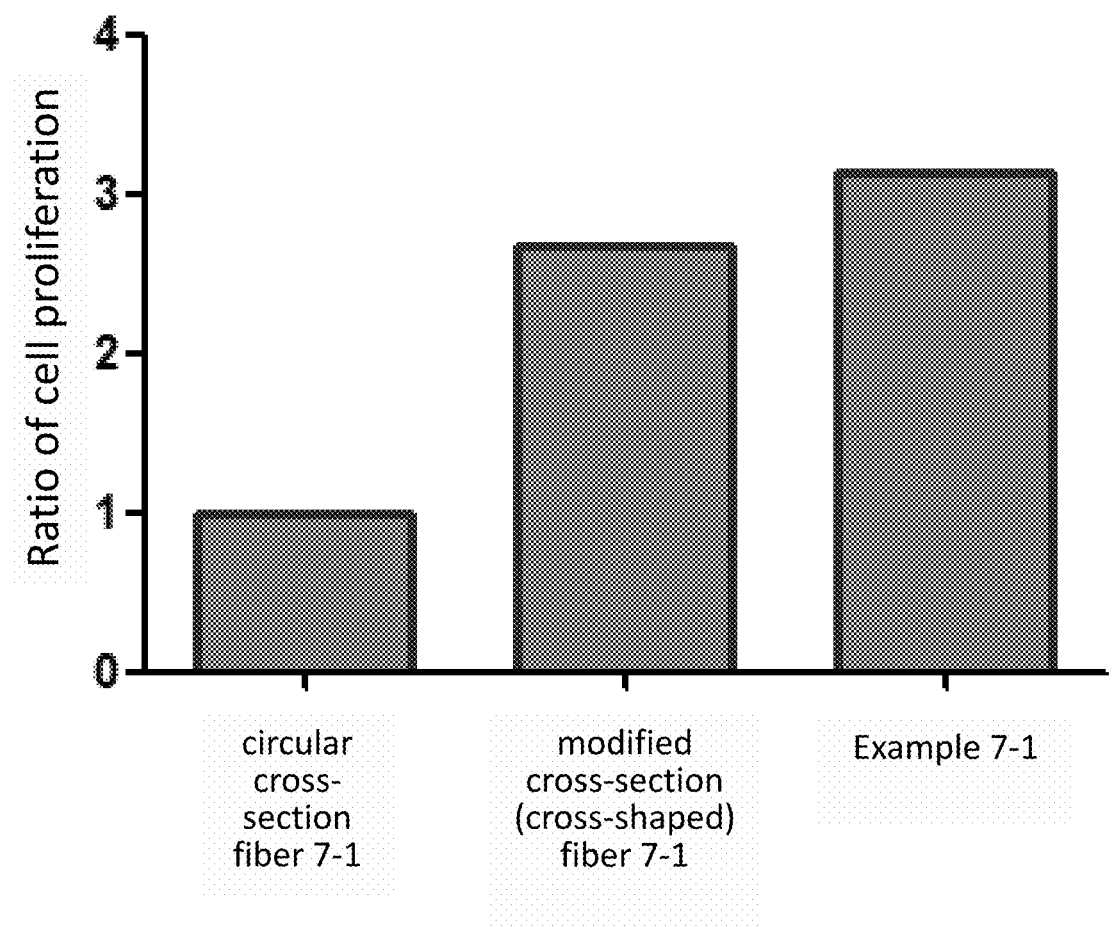
FIG. 4 is the bar chart of the cell proliferation ratio of the circular cross-section fiber 7-1, the modified cross-section (cross-shaped) fiber 7-1 and Example 7-1.

As shown in FIG. 4, under the condition of the same biodegradable materials and the same fiber outer diameter, the cell proliferation amount of Example 7-1 was slightly higher than that of the modified cross-section (cross-shaped) fibers 7-1 (untwisted). Therefore, the twisted state had the efficacy to improve cell adhesion.

Further, the space available for cell adhesion of Example 7-1 should be smaller than or equal to that of the modified cross-section (cross-shaped) fibers 7-1 (untwisted). As the cell proliferation amount of Example 7-1 was still higher, the twisted state can achieve unexpected efficacy of cell adhesion improvement.

(8) The Subcutaneous Implantation Study

Figure 5:
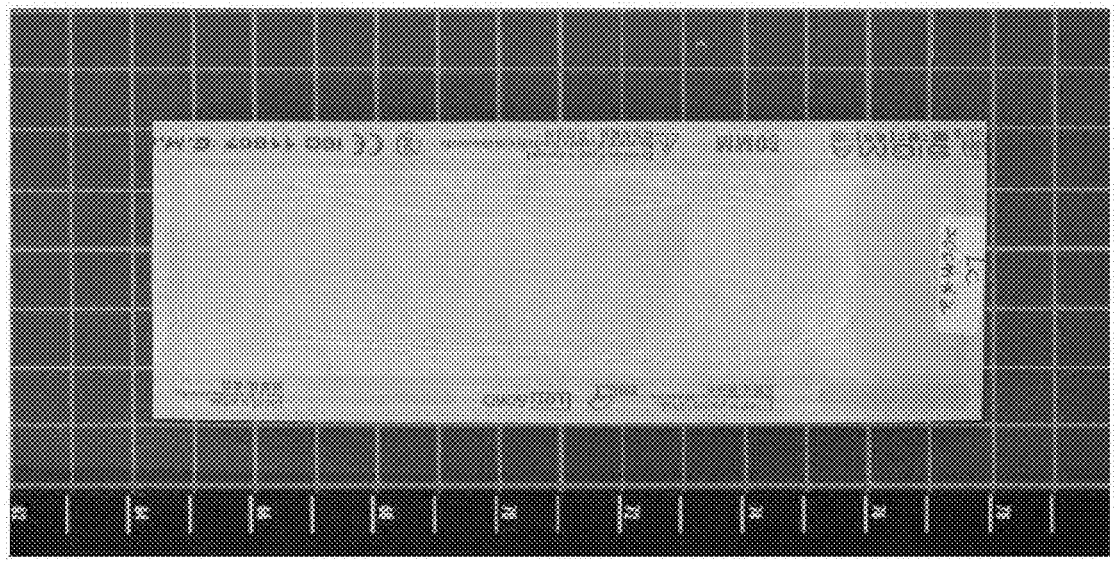
FIG. 5 is the photo of Example 2-5.
Figure 6:
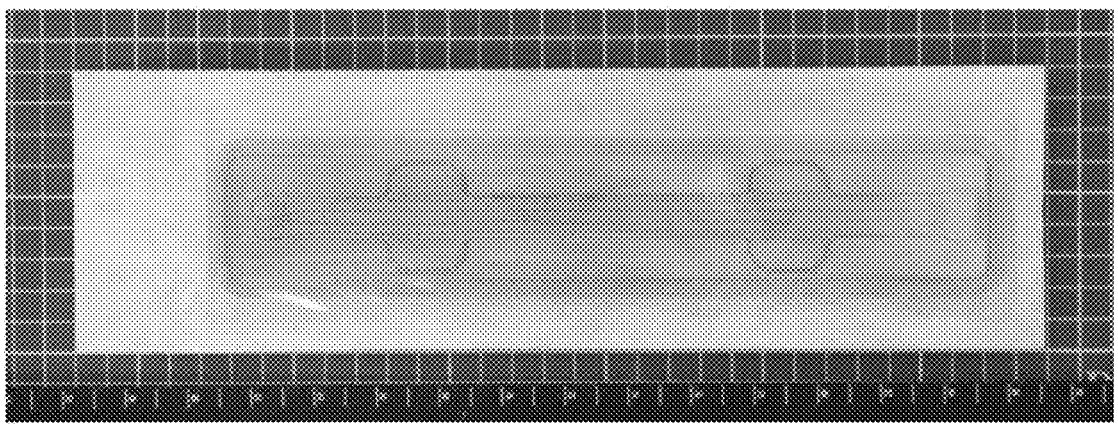
FIG. 6 is the photo of the commercial surgical thread for embedding (brand: MINT) (Comparative Example 1).

This study comprised: the twisted modified cross-section (cross-shaped) fiber: Example 2-5, which was shown in FIG. 5; wherein the biodegradable material thereof was PLC, the fiber outer diameter thereof was about 0.462 mm, and the fiber inner diameter thereof was about 0.143 mm, and Comparative Example 1, which was the commercial surgical thread for embedding (brand: MINT) and was shown in FIG. 6; wherein the biodegradable material thereof was PDO, and the fiber outer diameter thereof was USP1 (0.400 mm to 0.499 mm). Further, the manufacturing method of Example 2-5 was similar to that of Example 2-1, and the difference was that Example 2-5 had different fiber outer diameter and different fiber inner diameter.

This study was carried out according to ISO 10993-6: 2016 (Biological evaluation of medical devices—Part 6: Tests for local effects after implantation.) The experimental animals were two New Zealand White Rabbits in total, and were raised individually in separate cages during the experiment. The temperature of the environment was 19±3° C.; the humidity was 50±20%; and the light cycle was 12 hours light and 12 hours dark. The name of the feed is Prolab Rabbit Diet (brand: LabDiet, US), and the drinking water is RO water, both of which were supplied ad libitum.

Figure 7A:
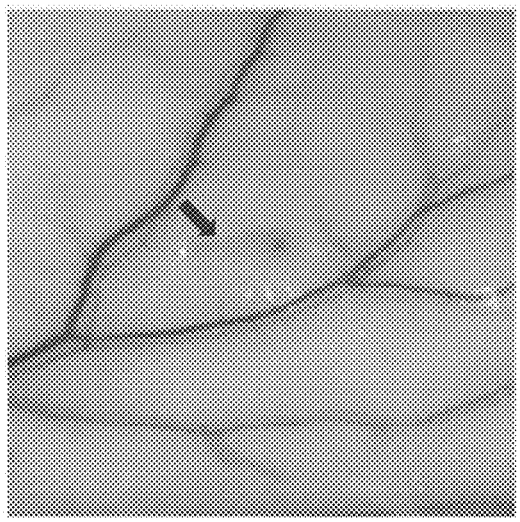
FIGS. 7A and 7B are the photos of the subcutaneous implantation of Example 2-5.
Figure 7B:
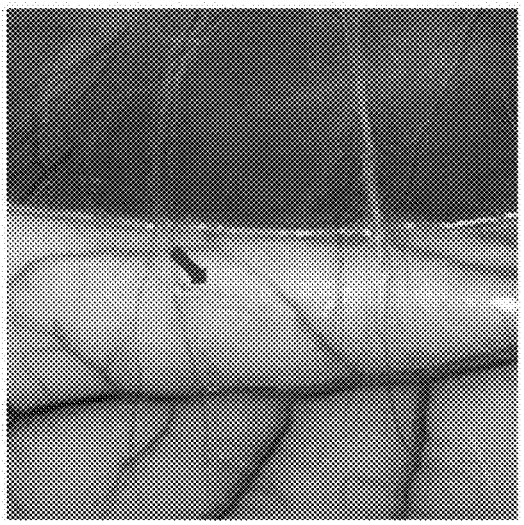
Figure 7C:
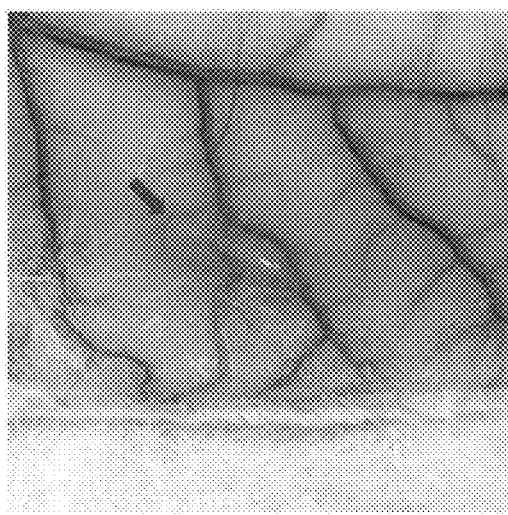
FIGS. 7C and 7D are the photos of the subcutaneous implantation of the commercial surgical thread for embedding (brand: MINT) (Comparative Example 1).
Figure 7D:
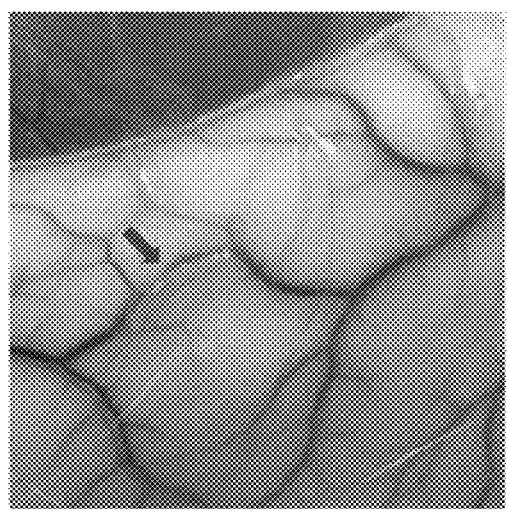

Example 2-5 was implanted into the subcutaneous site on the left side of the back of the two experimental animals, as shown and pointed out by the arrows in FIGS. 7A and 7B. Comparative Example 1 was implanted into the subcutaneous site on the right side of the back of the two experimental animals, as shown and pointed out by the arrows in FIGS. 7C and 7D.

After Example 2-5 and Comparative Example 1 were implanted for 28 days, the experimental animals were sacrificed, and the tissue samples at the implantation sites were collected, fixed, and preserved in 10% neutral buffered formalin for the subsequent hematoxylin and eosin stain and microscopic examination. The results were shown in FIGS.

8A to 8D; wherein the arrow pointed to the fibrous capsule, and the asterisk indicated the site of the focal collagen formation.

According to the histopathology evaluation format in ISO 10993-6:2016, the score for the inflammation indicators (polymorphonuclear, lymphocytes, plasma cells, macrophages, giant cells, necrosis), neovascularisation, fibrosis, fatty infiltrate, traumatic necrosis and foreign body debris were provided in order, and the results were shown in Table 7; wherein the "SUB-TOTAL" indicated "sum of score among groups"; and the "Average" indicated "sum of score among groups/the numbers of recognizable implantation sites," which was used to determine irritant ranking in the conclusion of the histopathological evaluation, and a negative difference was recorded as zero.

TABLE 7 the evaluation results of polymorphonuclear, lymphocytes, plasma cells, macrophages, giant cells, necrosis, neovascularisation, fibrosis, fatty infiltrate, traumatic necrosis and foreign body debris of Example 2-5 and Comparative Example 1

| Implantation site | Example 2-5 | | Comparative Example 1 | |
|---|---|---|---|---|
| number | T1 | T2 | C1 | C2 |
| Inflammation | score | | | |
| Polymorphonuclear | 1 | 1 | 1 | 1 |
| Lymphocyte | 1 | 1 | 2 | 2 |
| Plasma cells | 0 | 0 | 0 | 0 |
| Macrophage | 1 | 1 | 1 | 1 |
| Giant cells | 0 | 0 | 0 | 0 |
| Necrosis | 0 | 0 | 0 | 0 |
| SUB-TOTAL (×2) | 12 | | 16 | |
| Neovascularisation | 1 | 1 | 1 | 1 |
| Fibrosis | 1 | 1 | 2 | 2 |
| Fatty infiltrate | 0 | 0 | 0 | 0 |
| SUB-TOTAL | 4 | | 6 | |
| TOTAL | 16 | | 22 | |
| GROUP TOTAL | 16 | | 22 | |
| Average | 8.0-11.0 = −3.0 | | | |
| Traumatic necrosis | 0 | 0 | 0 | 0 |
| Foreign body debris | 0 | 0 | 0 | 0 |
| Conclusion | minimal or no reaction (0.0 to 2.9) | | | |

As shown in Table 7, Example 2-5 had a score of lymphocyte of 2 in total, which was lower than that of 4 of Comparative Example 1. Therefore, Example 2-5 had a lower inflammatory potential. Further, Example 2-5 had a score of fibrosis of 2 in total, which was lower than that of 4 of Comparative Example 1. Therefore, Example 2-5 had lower risk of incurring subcutaneous tissue fibrosis.

Further, the group total of Example 2-5 was 16, so the average thereof was 8; and the group total of Comparative Example 1 was 22, so the average thereof was 11. As the average of Example 2-5 was lower than that of Comparative Example 1, a negative difference was obtained and recorded as zero. Therefore, among the four irritant rankings: (1) minimal or no reaction (0.0 to 2.9); (2) slight reaction (3.0 to 8.9); (3) moderate reaction (9.0 to 15.0); and (4) severe reaction (15.1), Example 2-5 had the lowest irritant ranking: minimal or no reaction.

Figure 8A:
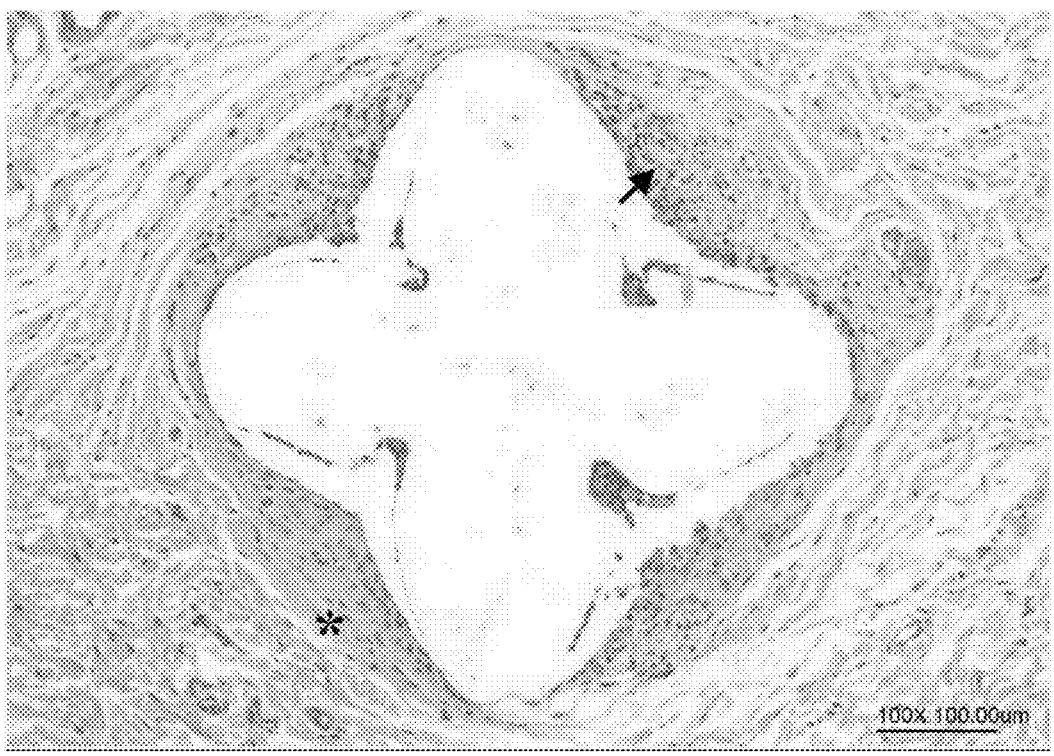
FIGS. 8A and 8B are the photos of the stained tissue sections of the subcutaneous implantation of Example 2-5.
Figure 8B:
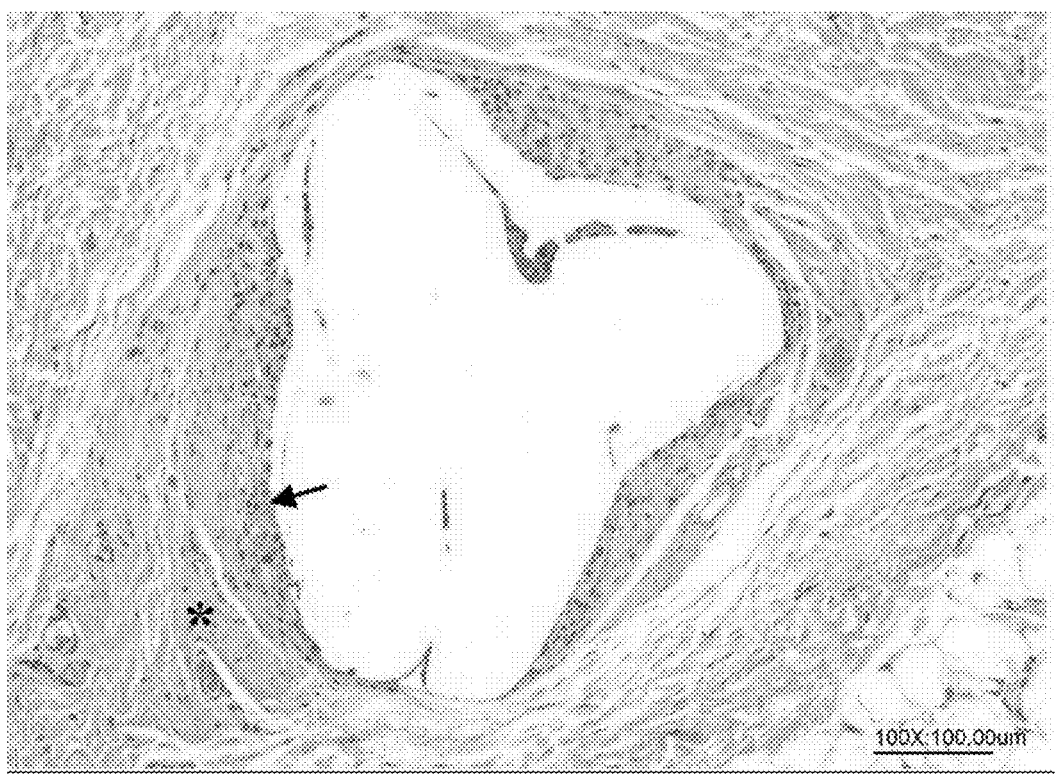
Figure 8C:
FIGS. 8C and 8D are the photos of the stained tissue sections of the subcutaneous implantation of Comparative Example 1.
Figure 8D:
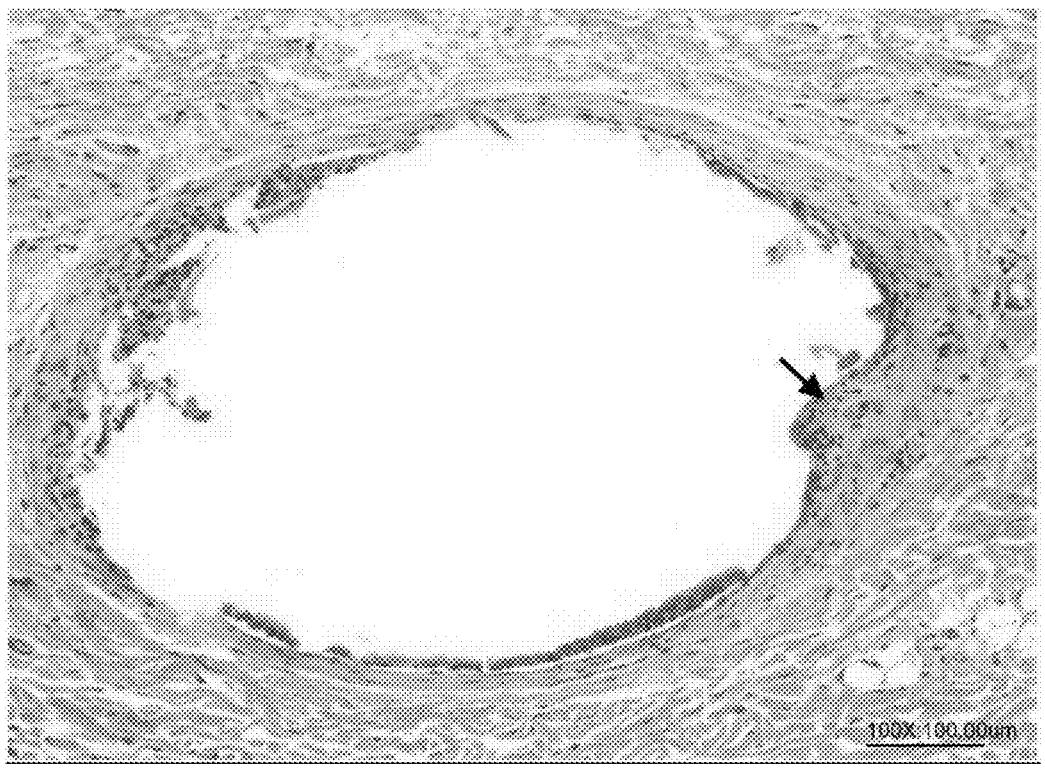

Further, as shown in FIGS. 8A and 8B, Example 2-5 was the single strand of the twisted modified cross-section (cross-shaped) fiber, so the hollow part of the tissue section in the photos showed the distinct shape of the protruding arm corresponding to the cross section of Example 2-5 of a cross shape, whereas the hollow part of the tissue section in FIGS. 8C and 8D was an oval-shape without the shape of the protruding arm.

Finally, FIGS. 8A and 8B were marked with the asterisk which indicated the site of the focal collagen formation, and no asterisk was marked in FIGS. 8C and 8D. Therefore, Example 2-5 had the efficacy of promotion of collagen formation, thereby improving the elasticity and firmness of the skin.

(9) Cytotoxicity Test

This test comprised: the original extract of Example 2-5 (Example 2-6), the 50% extract of Example 2-5 (Example 2-7), the original extract of Comparative Example 1 (Comparative Example 2), the blank, the negative control and the positive control, and followed ISO 10993-5:2009 (Biological evaluation of medical devices) and EN ISO 10993-5: 2009 to carry out the cytotoxicity test for the extracts of Example 2-5 and Comparative Example 1 (Example 2-6, Example 2-7 and Comparative Example 2).

A. The Preparation of the Extracts

I. Example 2-6, Example 2-7 and Comparative Example 2: According to the standard of ISO 10993-12:2021, the extraction ratio of the test article (Example 2-5 and Comparative Example 1) was that the surface of the test article/the volume of the culture medium shall be about 6 $cm^2$/mL, and the incubation was carried out at a rotation speed of 100 rpm under 37±1° C. for 24±2 h for extraction. After extraction, the original extracts of Example 2-5 and Comparative Example 1 were clear, particulate-free and without color change. Example 2-7 was obtained by doubling the culture medium of Example 2-6. Further, the culture medium was MEM alpha which comprised 10% (v/v) horse serum, 1% (v/v) penicillin-streptomycin solution, 1% (v/v) L-glutamine and 1% (v/v) non-essential amino acids.

II. The extracts of the blank, the negative control and the positive control: (1) the blank was obtained by incubating 5.0 mL of the culture medium at a rotation speed of 100 rpm under 37±1° C. for 24±2 h; (2) the negative control adopted high density polyethylene (HDPE). According to ISO 10993-12:2021, the ratio (the weight of the test article (HDPE)/the volume of the culture medium) was about 0.2 g/mL, so 1 g of HDPE was immersed in 5 mL of the culture medium, and incubated at a rotation speed of 100 rpm under 37±1° C. for 24±2 h; and (3) the positive control adopted Dimethyl sulfoxide (DMSO), and based on the total volume of DMSO and the culture medium, the concentration of DMSO was 10% (v/v). The culture medium with 10% (v/v) DMSO was incubated at a rotation speed of 100 rpm under 37±1° C. for 24±2 h.

B. Quantitative Analysis of Toxicity $1 \times 10^4$ of L929 mouse fibroblast cells were seeded in 96-well culture plates, and then incubated in the culture medium of MEM alpha at 37±1° C. in 5% $CO_2$ atmosphere for 24±2 h. Afterwards, the culture medium of MEM alpha in each well was removed and replenished with 0.5 mL of the corresponding extract of each group, wherein each group was carried out in triplicate, and subsequently incubated at 37±1° C. in 5% $CO_2$ atmosphere for 24±2 h. At the end of the incubation period, the extracts of each group were removed and replenished 0.1 mL of fresh culture medium in each well. 10 µL MTT reagent (kit component, 4890-25-01)

was further added into each well. The reaction was performed at 37° C. in 5% $CO_2$ atmosphere for 2 hours to 3 hours and kept from light, and then 0.1 mL of detergent reagent (kit component, 4890-25-02) was added into each well for further incubation in dark for 2 hours to 3 hours. Finally, the absorbance of each group was measured at 570 nm by a microplate reader (ELx800, BioTek); wherein the absorbance of the blank served as the basis for cell viability, which was provided as 100%. The results were shown in Table 8; wherein a cell viability <70% indicated that the group had a cytotoxic potential.

TABLE 8 the viabilities and mortalities of cells of the blank, the negative control, the positive control, Example 2-6, Example 2-7 and Comparative Example 2

| Group | Absorbance ($OD_{570\ nm}$) | Viability (%) | Mortality (%) |
| --- | --- | --- | --- |
| Blank | 1.160 ± 0.005 | 100 | 0 |
| Negative control | 1.039 ± 0.030 | 90 | 10 |
| Positive control | 0.198 ± 0.001 | 17 | 83 |
| Example 2-6 | 1.063 ± 0.021 | 92 | 8 |
| Example 2-7 | 1.088 ± 0.027 | 94 | 6 |
| Comparative Example 2 | 0.770 ± 0.021 | 74 | 26 |

As shown in Table 8, the cell viabilities of Example 2-6 and Example 2-7 were 92% and 94%, respectively, which were more than 70%, and indicated as no cytotoxicity according to ISO 10993-5:2009. Further, the cell viability of Example 2-6 of 92% was significantly higher than 74% of Comparative Example 2. Therefore, the surgical thread of the present invention had a higher safety than the commercial surgical threads for embedding.

C. Qualitative Analysis of Toxicity

This analysis comprised the blank, the negative control, the positive control, Example 2-6 and Comparative Example 2. For clarification, according to the results of the quantitative analysis of toxicity, Example 2-6 was safe, so Example 2-7 was not included in this analysis. This analysis comprised the steps as follows: $5 \times 10^4$ of L929 mouse fibroblast cells were seeded in 24-well culture plates, and then incubated in the culture medium of MEM alpha at 37±1° C. in 5% $CO_2$ atmosphere for 24±2 h. After cell adhesion was in a sub-confluent monolayer, the culture medium of MEM alpha in each well was removed and replenished with 0.5 mL of the corresponding extract of each group, wherein each group was carried out in triplicate, and subsequently incubated at 37±1° C. in 5% $CO_2$ atmosphere for 24±2 h. At the end of the incubation period, the cells in each group were stained with the neutral red solution, and the cell morphology was observed under an inverted microscope. The results were shown in FIG. 9.

Figure 9:
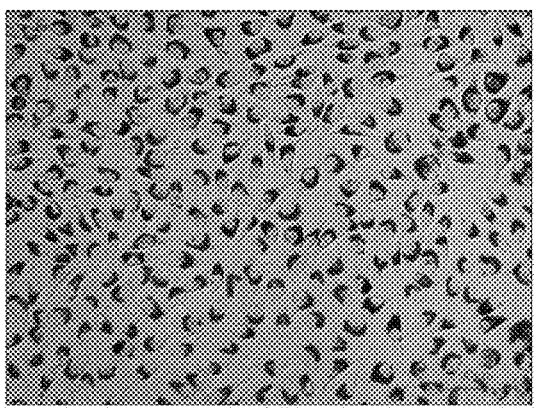
FIG. 9 shows the photos showing the cell growth status of the blank, the negative control, the positive control, Example 2-6 and Comparative Example 2.
Figure 9:
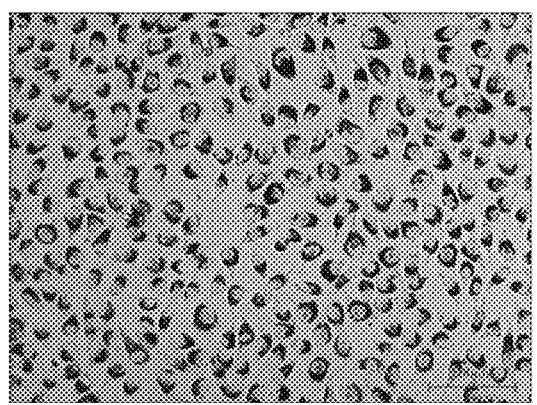
Figure 9:
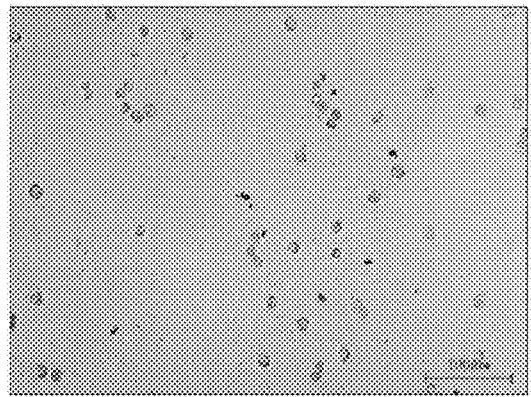
Figure 9:
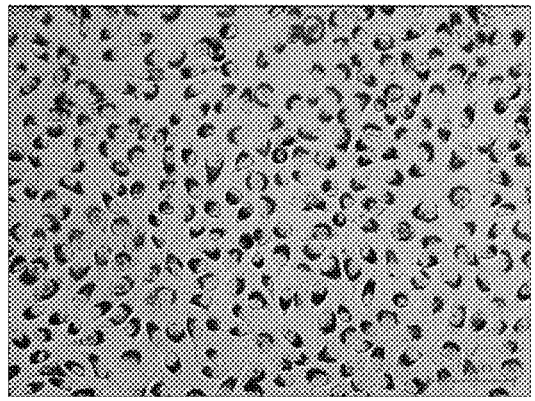
Figure 9:
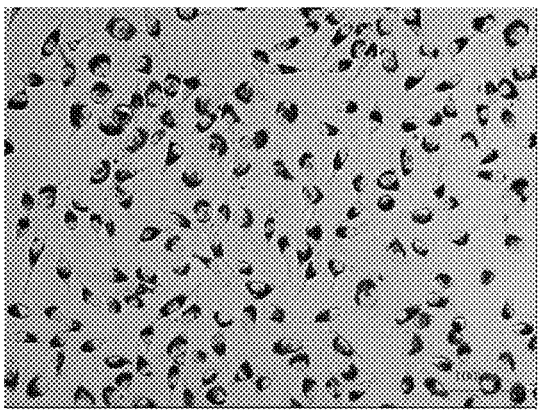

As shown in FIG. 9, the cell morphology of Example 2-6 was the same as those of the blank and the negative control, which indicated that the cells in Example 2-6 was as healthy as those in the blank and the negative control. Further, the cell morphology of Comparative Example 2 indicated a healthy status as well. However, the cell density of Comparative Example 2 was significantly lower than that of Example 2-6, and such result accorded with the aforementioned results of the quantitative analysis of toxicity.

(10) Pyrogen Study

This study was carried out according to USP 45/NF40: 2022 <151> and ISO/TR 21582:2021. The experimental animals were three male New Zealand White Rabbits, so this study was carried out in triplicate, and the original extract of Example 2-5 (Example 2-8) was injected intravenously into the ear vein of each rabbit with a single dose of 10 ml/kg.

Example 2-8: according to ISO 10993-12:2021, the ratio (the surface of the test article (Example 2-5)/the volume of saline) was about 6 $cm^2$/mL, and Example 2-5 was immersed in saline, and incubated at a rotation speed of 100 rpm under 50±2° C. for 72±2 h for extraction. After extraction, the original extract of Example 2-5 (Example 2-8) was clear, particulate-free and without color change.

The body weight of each experimental animal was measured before the injection of Example 2-8 to determine the injection volume, and the body temperature of each experimental animal was also measured and served as the basis. Further, the body temperatures thereof were measured at 1 hour, 1.5 hours, 2 hours, 2.5 hours and 3 hours after the injection of Example 2-8.

The result was that the body temperatures of the three male New Zealand white rabbits increased by 0.21° C., 0.11° C. and 0.24° C. respectively. As such temperature change was lower than 0.5° C., Example 2-8 passed the pyrogen test according to USP 45/NF40: 2022 <151> or ISO/TR 21582: 2021, which indicated that the surgical thread of Example 2-5 did not have pyrogens.

(11) Acute Systemic Toxicity Study

This study was carried out according to ISO 10993-11: 2017. The experimental animals were male ICR mice, and this study comprised four groups: (1) the control group with a polar vehicle: Intravenous injection (I.V. injection) of saline; (2) the experimental group with a polar vehicle: I.V. injection of the original extract of Example 2-5 (Example 2-9) obtained by immersing Example 2-5 in saline; (3) the control group with a non-polar vehicle: intraperitoneal injection (I.P. injection) of cottonseed oil; and (4) the experimental group with a non-polar vehicle: I.P. injection of the original extract of Example 2-5 (Example 2-10) obtained by immersing Example 2-5 in cottonseed oil.

Example 2-9: According to ISO 10993-12:2021, the ratio (the surface of the test article (Example 2-5)/the volume of saline) was about 6 $cm^2$/mL, and Example 2-5 was immersed in saline, and incubated at a rotation speed of 100 rpm under 50±2° C. for 72±2 h for extraction. After extraction, the original extract of Example 2-5 (Example 2-9) was clear, particulate-free and without color change.

Example 2-10: According to ISO 10993-12:2021, the ratio (the surface of the test article (Example 2-5)/the volume of cottonseed oil) was about 6 $cm^2$/mL, and Example 2-5 was immersed in cottonseed oil, and incubated at a rotation speed of 100 rpm under 50±2° C. for 72±2 h for extraction. After extraction, the original extract of Example 2-5 (Example 2-10) was clear, particulate-free and without color change.

Each group had five experimental animals, and each experimental animal was injected with a single dose of 50 ml/kg. All experimental animals were observed for the determination of toxicity reaction or death immediately after injection and at $4^{th}$, $24^{th}$, $48^{th}$ and $72^{nd}$ hour after injection. The results showed that no toxicity reaction or death was observed in all groups, so Example 2-9 and Example 2-10 passed acute systemic toxicity study, which indicated that the surgical thread of Example 2-5 had no acute systemic toxicity.

(12) Intracutaneous Irritation Study

This study was carried out according to ISO 10993-23: 2021 (Part 23: Biological evaluation of medical devices Tests for irritation). The experimental animals were male New Zealand White Rabbits, and this study comprised four groups: (1) the control group with a polar vehicle: Injection of saline on the back of the experimental animal; (2) the experimental group with a polar vehicle: Injection of the original extract of Example 2-5 (Example 2-11) obtained by immersing Example 2-5 in saline on the back of the experimental animal; (3) the control group with a non-polar vehicle: Injection of cottonseed oil on the back of the experimental animal; and (4) the experimental group with a non-polar vehicle: Injection of the original extract of Example 2-5 (Example 2-12) obtained by immersing Example 2-5 in cottonseed oil on the back of the experimental animal; wherein Example 2-11 was the same as Example 2-9, and Example 2-12 was the same as Example 2-10.

Figure 10A:
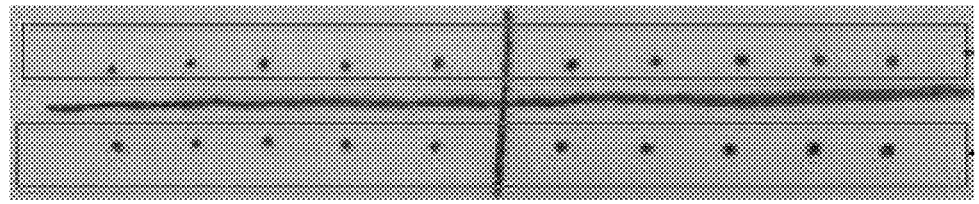
FIGS. 10A to 10C are the dorsal photos of the experimental animals at different time, which shows the results at $24^{th}$, $48^{th}$ and $72^{nd}$ hour after injection in order of the control group with a polar vehicle, the experimental group with a polar vehicle (Example 2-11 was injected), the control group with a non-polar vehicle, and the experimental group with a non-polar vehicle (Example 2-12 was injected).
Figure 10B:
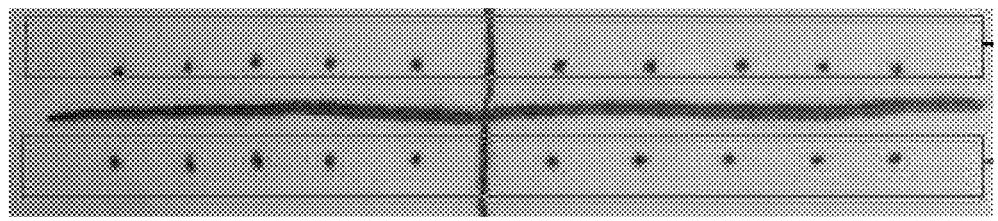
Figure 10C:
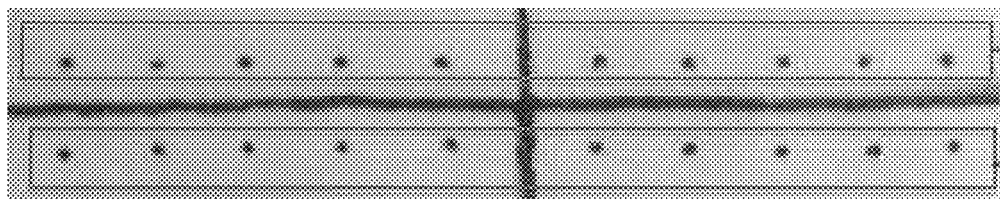

Each group was injected with a single dose of 0.2 ml for one injection site, and there were five injection sites for each group. All experimental animals were observed for the determination of intracutaneous/intradermal reaction immediately after injection and at $24^{th}$, $48^{th}$ and $72^{nd}$ hour after injection. The photos of the results at $24^{th}$, $48^{th}$ and $72^{nd}$ hour after injection were shown in FIGS. 10A to 10C; wherein the 5 points in the upper left part in each photo were the control group with a polar vehicle; those in the upper right part were the control group with a non-polar vehicle; those in the lower left part were the experimental group with a polar vehicle, where Example 2-11 was injected; and those in the lower left part were the experimental group with a non-polar vehicle, where Example 2-12 was injected. As shown in FIGS. 10A to 10C, each group showed no intracutaneous/intradermal reaction, so Example 2-11 and Example 2-12 passed the intracutaneous irritation study. Therefore, the surgical thread of Example 2-5 had no intradermal irritation potential.

To sum up, the surgical thread of the present invention has the following advantages: (1) increasing the surface, thereby reserving a space for additional additives and the cell adhesions in the tissue; (2) increasing the coefficient of kinetic friction for adhering to or staying in the tissue for a longer period, thereby enhancing the cosmetic efficacy; (3) reducing the weight burden on the face of the patients after the implantation of the surgical thread; (4) increasing the softness of the surgical thread, thereby increasing the popularity in clinical applications; (5) improving cell adhesion and proliferation; (6) promotion of collagen formation, thereby improving the elasticity and firmness of the skin; (7) good safety, comprising: no inflammatory potential, no cytotoxicity, no pyrogen, no acute systemic toxicity and no intradermal irritation potential.

What is claimed is:

1. A method for cosmetic treatment, comprising embedding a surgical thread within a subject in need thereof, wherein the surgical thread comprises a modified cross-section fiber, the modified cross-section fiber is in a twisted state, the twisted state is obtained by twisting the modified cross-section fiber, and the surgical thread has an amount of twist of 10 TPM (twist per meter) to 1500 TPM.

2. The method for cosmetic treatment as claimed in claim 1, wherein the modified cross-section fiber has a cross-section in a cross shape, a Y shape, a Union Jack shape or a multi-leaf shape.

3. The method for cosmetic treatment as claimed in claim 2, wherein a site for embedding the surgical thread is within a face of the subject.

4. The method for cosmetic treatment as claimed in claim 1, wherein the twisted state has a twisting direction of a clockwise direction, a counterclockwise direction or a combination thereof.

5. The method for cosmetic treatment as claimed in claim 1, wherein the surgical thread has a coefficient of kinetic friction of equal to or more than 0.35.

6. The method for cosmetic treatment as claimed in claim 5, wherein a site for embedding the surgical thread is within a face of the subject.

7. The method for cosmetic treatment as claimed in claim 1, wherein the modified cross-section fiber has a fiber inner diameter and a fiber outer diameter, and the ratio of the fiber inner diameter to the fiber outer diameter is 0.1 to 0.95.

8. The method for cosmetic treatment as claimed in claim 7, wherein a site for embedding the surgical thread is within a face of the subject.

9. The method for cosmetic treatment as claimed in claim 1, wherein the surgical thread has a density of 0.1 g/cm3 to 1.1 g/cm3.

10. The method for cosmetic treatment as claimed in claim 9, wherein a site for embedding the surgical thread is within a face of the subject.

11. The method for cosmetic treatment as claimed in claim 1, wherein the surgical thread has a tensile strength of 2.4 N to 100 N.

12. The method for cosmetic treatment as claimed in claim 11, wherein a site for embedding the surgical thread is within a face of the subject.

13. The method for cosmetic treatment as claimed in claim 1, wherein the surgical thread has an elongation rate of 10% to 150%.

14. The method for cosmetic treatment as claimed in claim 13, wherein a site for embedding the surgical thread is within a face of the subject.

15. The method for cosmetic treatment as claimed in claim 1, wherein the modified cross-section fiber has an ingredient of a biodegradable material, and the biodegradable material comprises polydioxanone, poly(L-lactide-co-caprolactone), poly(L-lactide) or poly(glycolide-co-L-lactide).

16. The method for cosmetic treatment as claimed in claim 1, wherein the modified cross-section fiber further comprises an additive, and the additive comprises an antibacterial ingredient, an active ingredient or a combination thereof.

17. The method for cosmetic treatment as claimed in claim 1, wherein a site for embedding the surgical thread is within a face of the subject.

* * * * *